(12) United States Patent
Kippersund et al.

(10) Patent No.: US 10,557,731 B2
(45) Date of Patent: Feb. 11, 2020

(54) SENSOR APPARATUS AND METHOD FOR MEASURING FLOW

(71) Applicant: XSENS AS, Bergen (NO)

(72) Inventors: Remi Andre Kippersund, Bergen (NO); Magne Kjetil Husebø, Tertnes (NO); Per Lunde, Sandsli (NO); Kjell-Eivind Frøysa, Fryllingsdalen (NO); Peter Thomas, Rådal (NO); Kjetil Daae Lohne, Bønes (NO); Jon Oddvar Hellevang, Bergen (NO)

(73) Assignee: XSENS AS, Bergen (NO)

( * ) Notice: Subject to any disclaimer, the term of this patent is extended or adjusted under 35 U.S.C. 154(b) by 562 days.

(21) Appl. No.: 15/108,513

(22) PCT Filed: Dec. 29, 2014

(86) PCT No.: PCT/EP2014/003473
§ 371 (c)(1),
(2) Date: Jun. 27, 2016

(87) PCT Pub. No.: WO2015/096901
PCT Pub. Date: Jul. 2, 2015

(65) Prior Publication Data
US 2016/0327419 A1 Nov. 10, 2016

(30) Foreign Application Priority Data
Dec. 27, 2013 (GB) .................................. 1323076.8

(51) Int. Cl.
*G01F 1/66* (2006.01)
*G01F 1/74* (2006.01)
(Continued)

(52) U.S. Cl.
CPC ................ *G01F 1/662* (2013.01); *G01F 1/66* (2013.01); *G01F 1/663* (2013.01); *G01F 1/667* (2013.01);
(Continued)

(58) Field of Classification Search
CPC . G01F 1/662; G01F 1/66; G01F 1/663; G01F 1/667; G01F 1/74; G01N 29/22
(Continued)

(56) References Cited

U.S. PATENT DOCUMENTS 3,552,190 A * 1/1971 Lefebvre ................ G01N 29/27
73/610
3,973,152 A 8/1976 Karplus
(Continued)

FOREIGN PATENT DOCUMENTS

CN 203132615 U 8/2013
DE 102011015677 A1 10/2012
(Continued)

OTHER PUBLICATIONS

Balvantin, A., et al., "A Study of Helical Lamb Wave Propagation on Two Hollow Cylinders with Imperfect Contact Conditions", American Institute of Physics Conference Proceedings, vol. 1511, Jul. 15-20, 2002, pp. 67-74.
(Continued)

*Primary Examiner* — Tarun Sinha
(74) *Attorney, Agent, or Firm* — Arent Fox LLP

(57) ABSTRACT

A sensor apparatus is provided for measuring within a region of a conduit for guiding a flow. The apparatus includes a transducer arrangement disposed at least partially around an external surface of a wall of the conduit and having one or more driver elements for exciting in operation a helical acoustic wave propagation within the wall of the conduit for leaking acoustical energy from the helical acoustic wave
(Continued)

propagation over an extensive area of the wall of the conduit for stimulating waves in chordal paths within the flow, wherein the waves in the choral paths within the flow re-enter the wall of the conduit to propagate further as a guided helical wave. The transducer arrangement includes one or more sensors for receiving a re-entered portion of the acoustic wave propagation along the paths within the flow which interacts with the flow and includes information characterizing properties of the flow.

19 Claims, 27 Drawing Sheets

(51) Int. Cl.
    *G01P 5/00*      (2006.01)
    *G01N 29/22*      (2006.01)

(52) U.S. Cl.
    CPC ............... *G01F 1/74* (2013.01); *G01N 29/22* (2013.01); *G01P 5/001* (2013.01); *G01N 2291/0289* (2013.01); *G01N 2291/02433* (2013.01)

(58) Field of Classification Search
    USPC .......................................................... 73/597
    See application file for complete search history.

(56) References Cited

U.S. PATENT DOCUMENTS

| | | | | |
|---|---|---|---|---|
| 4,102,186 A | * | 7/1978 | Brown | G01F 1/667 73/861.27 |
| 4,462,261 A | | 7/1984 | Keyes et al. | |
| 5,765,596 A | * | 6/1998 | LaHaye | F16L 9/18 138/110 |
| 6,089,104 A | | 7/2000 | Chang | |
| 6,626,043 B1 | * | 9/2003 | Bailey | G01L 1/246 250/227.21 |
| 7,302,861 B2 | | 12/2007 | Winston et al. | |
| 7,336,862 B1 | | 2/2008 | Xai et al. | |
| 2002/0053243 A1 | | 5/2002 | Su | |
| 2003/0121335 A1 | | 7/2003 | Liu et al. | |
| 2004/0123666 A1 | * | 7/2004 | Ao | G01F 1/662 73/644 |
| 2006/0144162 A1 | * | 7/2006 | Batzinger | F22B 37/38 73/861.25 |
| 2007/0125175 A1 | * | 6/2007 | Junker | G01N 29/041 73/592 |
| 2007/0175280 A1 | | 8/2007 | Johansen | |
| 2008/0156107 A1 | | 7/2008 | Ao et al. | |
| 2011/0271769 A1 | | 11/2011 | Kippersund et al. | |

FOREIGN PATENT DOCUMENTS

| | | | |
|---|---|---|---|
| FR | 2781047 | A1 | 1/2000 |
| GB | 2399412 | A | 9/2004 |
| GB | 2412966 | A | 10/2005 |
| WO | 98/19296 | A1 | 5/1998 |
| WO | 2008/073673 | A1 | 6/2008 |
| WO | 2010/118793 | A1 | 10/2010 |

OTHER PUBLICATIONS

Leonard, Kevin, et al., "Guided Wave Helical Ultrasonic Tomography of Pipes", The Journal of the Acoustical Society of America, vol. 114, No. 2, Aug. 2003, pp. 767-774.

Liu, W., et al., "Three-Dimensional Lamb Wave Propagation Excited by a Phased Piezoelectric Array", IPO Publishing, Smart Materials and Structures, vol. 19, Issue 8, Jun. 22, 2010, pp. 1-12.

International Search report and Written Opinion received for International Patent Application No. PCT/EP2014/003473, dated Apr. 30, 2015, 13 pages.

Written Opinion received for International Patent Application No. PCT/EP2014/003473, dated Mar. 10, 2016, 5 pages.

Combined Search and Examination Report received for United Kingdom Patent Application No. GB1323076.8, dated Apr. 8, 2014, 8 pages.

* cited by examiner

SENSOR APPARATUS AND METHOD FOR MEASURING FLOW

TECHNICAL FIELD

The present disclosure relates to sensor apparatus for measuring flow, for example to sensor apparatus for measuring complex flows, for example stratified flows, laminar to turbulent flows, swirl-type flows, asymmetrical flows and similar. Moreover, the disclosure concerns methods of using aforesaid sensor apparatus for measuring flow, for example to methods of measuring aforesaid complex flow. Furthermore, the disclosure relates to computer program products comprising a non-transitory computer-readable storage medium having computer-readable instructions stored thereon, the computer-readable instructions being executable by a computerized device comprising processing hardware to execute aforesaid methods.

BACKGROUND

Many situations in industry, for example in chemical industries, nuclear power industries, and oil and gas industries including downhole and subsea applications, require measurement of a flow rate of a fluid through a conduit, for example through a pipe. Moreover, when a temperature measurement and a pressure measurement across an orifice, through which the fluid flows, are made, it is feasible to infer a density and a viscosity of the fluid, for example via performing computations. However, an issue of measurement accuracy arises when the fluid flow is turbulent and/or is spatially inhomogeneous. Situations of spatial non-homogeneity arise, for example in petrochemicals industries wherein fluids pumped from an oil well often include a mixture of oil, water, gas and sand particles. Moreover, physical characteristics of such a flow are susceptible to changing considerably on an onset of turbulent flow. Many known reported flow measuring apparatus are designed to cope with non-turbulent flows, and will potentially generate erroneous flow measurements when confronted with complex flows, for example turbulent flows. There is a contemporary need for highly accurate non-invasive flow measuring apparatus for monitoring flows of crude oil containing fractions of water and/or gas.

In a published European patent document EP 2 431 716A1 ("A multiphase flow meter and a correction method for such a multiphase flow meter", Applicant—Services Petroliers Schlumberger, Paris, France; inventors—Lupeau & Baker), there is described a flow meter for measuring a flow rate of a multiphase fluids mixture comprising at least one gas phase and one liquid phase, wherein the flow meter comprises:

(i) a pipe section through which the multiphase fluid mixture flows comprising a throat between an upstream part and a downstream part such as to generate a pressure drop between the upstream part and the downstream part; and
(ii) a fraction measuring device for estimating a fractional flow rate for each phase of the multiphase fluid mixture passing through the throat.

The flow meter further comprises at least one ultrasonic sensor which is operable to estimate a thickness of the liquid phase flowing as a liquid film along the wall of the pipe section, wherein the thickness is used to correct the estimated fractional flow rate for each phase when a gas liquid fraction (GLF) pertaining to the multiphase fluid mixture is such that the gas phase flows in a core of the pipe section, and the liquid phase flows along the wall of the pipe as the liquid film.

Referring to FIG. 1, an off-shore environment is indicated generally by 10, wherein a sea-bed assembly 30 is submerged in water 20, and is coupled via one or more sea-bed pipelines 40 to a petrochemicals processing facility 50. The assembly 30 is alternatively, or additionally, coupled via the one or more pipelines 40 to a floating oil platform (not shown). The sea-bed assembly 30 is coupled via a bore hole 60, for example defined by a liner tube, to a subterranean anticline including oil and/or gas resources. In many situations, the sea-bed assembly 30 is more than 1 km deep in the water 20 and is potentially subject to a pressure of 150 Bar or more. It is desirable to measure to a high accuracy a flow rate of a complex fluid being drawn up through the bore hole 60, for example. However, an environment experienced by the sea-bed assembly 30 is challenging for any type of precision flow meter. Although flow through the bore hole 60 may, for example, often be substantially non-turbulent, potential situations can be arise where highly turbulent flow rates can occur, for example in a event of a leak or unexpected pressure surge from the anticline, wherein it is highly desirable to be able to measure flow rates of complex fluids, even under turbulent conditions. Known types of flow meter are not able to provide such measurement flexibility and yet be able to withstand, over a long period of use, harsh environmental conditions associated with operation of the sea-bed assembly 30.

In a published US patent document US2008/163700A1 (Huang Songming), there is described a measuring apparatus for measuring properties of a flow of a fluid within a conduit including one or more walls, wherein the apparatus includes a transducer arrangement including transducers for emitting and receiving ultrasonic radiation in upstream and downstream directions in respect of the flow of fluid, and a signal processing arrangement for generating signals to excite the transducer arrangement and for processing received signals provided by the transducer arrangement for generating output signals from the signal processing arrangement indicative of properties of the flow. Moreover, there is also disclosed for the upstream and downstream directions that the apparatus is operable to perform measurements along first and second paths associated with each of the directions; for the first path, the transducer arrangement in cooperation with the conduit is operable to provide the first path solely via the one or more walls for Lamb-wave ultrasonic radiation coupling directly from a transducer for emitting ultrasonic radiation to a transducer for receiving ultrasonic radiation to generate a first received signal. Furthermore, for the second path, the transducer arrangement in cooperation with the conduit is operable to provide the second path for propagation of ultrasonic radiation within the one or more walls via Lamb waves coupling to at least a portion of the flow to propagate through the flow from a transducer for emitting ultrasonic radiation to a transducer for receiving ultrasonic radiation to generate a second received signal. The signal processing arrangement is operable to determine from the first and second signals ultrasonic radiation propagation time period through the first path and through the second path in each of the upstream and downstream flow directions, and to perform computational operations in respect of at least one of: a flow velocity (v) of the fluid in the conduit, a velocity of sound (c) through the fluid. Another published United States patent application US2008/163692A1 (Huang Songming) also describes a generally similar type of apparatus to that described in the aforesaid US patent application US2008/163700A1.

In a United Kingdom patent document GB2 399 412A ("Multiple phase fraction meter having compliant mandrel deployed within fluid conduit", Applicant—Weatherford/Lamb Inc.), there is described a hollow mandrel which is deployable within a production pipeline at least partly within a length of a speed-of-sound or phase-fraction meter. Sensors of the meter comprise Bragg gratings and wraps of fibre optic cable whose lengths are sensitive to acoustic pressure disturbances in the pipeline. A passive fibre optic based flow velocity meter is thereby provided, and the mandrel is optionally shaped to form an annular venture meter to provide an alternative implementation for calculating the fluid mixture density for purposes of double checking or calibration.

In a published PCT patent document WO 2008/073673A1 ("Ultrasonic Flow Rate Measurement using Doppler Frequency", Applicant—General Electric Company), there is described a method of determining a flow rate of a fluid in a conduit. Ultrasonic energy is directed through the conduit along multiple paths. The ultrasonic energy is detected and measured using a range-gated Doppler technique to determine the velocity of the fluid at several points in the conduit. The point velocities are used to calculate the average flow rate of the fluid in the conduit.

In a published U.S. Pat. No. 6,047,602 ("Ultrasonic buffer/waveguide", Applicant—Panametrics Inc.), there is described a waveguide for coupling ultrasonic energy from a source on one side of a fluid-bounding wall, such as a conduit, into fluid on the other side of the wall. The waveguide has a buffer that couples to the source, and a seat with an exit face, and an intermediate portion includes a redirecting surface for internally redirecting energy propagated along the buffer towards the exit face to exit as a narrow directed beam. The waveguide core has a rectangular cross-section which is narrow, namely has an aspect ratio above two, and the buffer has a length which is effective to isolate thermally and to protect the source from the conduit. The waveguide is attached via clamp-on or welding to a pipe or spool-face. Optionally, the buffer is a thin tube which couples shear waves into the seat portion, which has a rectangular cross-section.

In a published United States patent document U.S. Pat. No. 7,185,547B2 ("Extreme temperature clamp-on flow meter transducer", Applicant—Siemens Energy and Automation Inc.), there is described a device for measuring flow in a pipe. The device includes a first metal plate mounted to the pipe. The first metal plate includes a first contact portion for contacting a wall of the pipe and a first away portion spaced apart from the wall of the pipe. The device further includes a second plate including a second contact portion spaced apart from the wall of the pipe. A first transducer is mounted to the first away portion. Moreover, a second transducer is mounted to the second away portion. The first and second transducers are thereby mounted spatially remotely from the wall of the pipe.

In a published U.S. Pat. No. 8,090,131 B2 ("Steerable acoustic waveguide", Applicant—Elster NV/SA), there is described a steerable acoustic waveguide apparatus which includes a plurality of plates arranged in one or more linear arrays. Steering of an acoustic beam radiated from the waveguide apparatus may be achieved through differential delays of acoustic signals resulting from differences in timing, frequency, or mode or resulting from difference in physical attributes of the plates. The waveguide apparatus serves as a thermal buffer, and may simplify access to an acoustic path in a device such as an ultrasonic flow meter.

SUMMARY

The present disclosure seeks to provide an improved apparatus for measuring flow, for example for measuring flows of complex mixtures, both in non-turbulent and turbulent conditions, as well as coping with spatial non-homogeneity in the aforesaid complex mixtures.

Moreover, the present disclosure seeks to provide a method of using an improved apparatus for measuring flow, for example for measuring flows of complex mixtures both in non-turbulent and turbulent conditions, as well as coping with spatial non-homogeneity in the aforesaid complex mixtures.

Furthermore, the present disclosure seeks to provide a non-invasive meter accommodating a 0% to 100% gas-volume-fraction (GVF) measurement range, and providing measurement errors conforming to at least fiscal standards when operating in a single-phase mode.

According to a first aspect, there is provided a sensor apparatus for measuring within a region of a conduit for guiding a flow, wherein the sensor apparatus includes a transducer arrangement disposed at least partially around an external surface of a wall of the conduit, characterized in that the transducer arrangement includes one or more driver elements for exciting in operation a helical acoustic wave propagation within the wall of the conduit for leaking acoustical energy from the helical acoustic wave propagation over an extensive area of the wall of the conduit for stimulating waves in chordal paths within the flow, wherein the waves in the choral paths within the flow re-enter the wall of the conduit to propagate further as a guided helical wave;

the transducer arrangement includes one or more sensors for receiving a re-entered portion of the acoustic wave propagation along the chordal paths within the flow which interacts with the flow and which includes information which characterizes properties of the flow; and the transducer arrangement is operable to perform at least one of: switching between selected acoustic wave modes present in the acoustic wave propagation, steering an acoustic propagation direction of the acoustic wave propagation in a range lying between axial and radial directions relative to a central axis of the conduit.

The invention is of advantage in that the sensor apparatus is capable of measuring flows of complex mixtures and spatially inhomogeneous mixtures more accurately on account of interrogating the flows in a more comprehensive manner using acoustic radiation.

Methods of interrogating a flow in upstream and downstream directions by way of performing a differential measurement are described in an international PCT patent application PCT/NO2010/000480 (Tecom AS and Christian Michelsen Research AS), the contents of which are hereby incorporated by reference, for use in the sensor apparatus.

Optionally, in the sensor apparatus, the acoustic propagation direction of the acoustic wave propagation includes axial and radial directions relative to a central axis of the conduit.

Optionally, in the sensor apparatus, the transducer arrangement includes an elongate waveguide arrangement which is operable to support a helical mode acoustic wave propagation therein from the one or more driver elements disposed at one or more ends of the waveguide arrangement.

More optionally, in the sensor apparatus, the waveguide arrangement includes an acoustic radiation damping arrangement for dampening back-and-forth acoustic wave propagation namely arising from reflections at ends of the waveguide arrangement, along the waveguide arrangement. More optionally, in the sensor apparatus, the acoustic radiation damping arrangement is implemented by applying acoustic dampening material to the waveguide arrangement and/or by employing active damping of acoustic radiation.

Optionally, in the sensor apparatus, the waveguide arrangement includes a waveguide having a rectangular cross-section. More optionally, the waveguide arrangement has an aspect ration in a range of 1:1 to 1:10.

Optionally, in the sensor apparatus, the transducer arrangement includes one or more driver elements disposed in a phased array configuration, wherein the one or more driver elements are operable to provide steerable beams of acoustic radiation within an inner volume of the conduit when in operation.

Optionally, in the sensor apparatus, the transducer arrangement includes a monitoring arrangement which is implemented using one or more additional sensors attached to the waveguide arrangement to measure acoustic wave propagation direction and/or amplitude within the waveguide arrangement.

Optionally, in the sensor apparatus, the waveguide arrangement is implemented as a sheet, a collar, a helical elongate member, a helical strip, a structure formed integrally into the wall of the conduit.

Optionally, in the sensor apparatus, the waveguide arrangement includes a waveguide for interfacing to the wall of the conduit, whose thickness and waveguide material are mutually substantially similar to a thickness and a material of the wall of the conduit.

Optionally, in the sensor apparatus, the transducer arrangement includes one or more sensors which are implemented optically using one or more optical fibres, wherein one or more Bragg gratings are including along the one or more optical fibres for rendering the one or more optical fibres sensitive. More optionally, in the sensor apparatus, the one or more optical fibres are implemented using at least one of: one or more fused silica optical fibres, one or more sapphire optical fibres. More optionally, the optical fibres are monomode fibres.

Optionally, in the sensor apparatus, the waveguide arrangement is detachable from the wall of the conduit.

Optionally, in the sensor apparatus, the waveguide arrangement further includes a thermal radiation shielding arrangement and/or an ionization shielding arrangement for at least partially shielding the one or more driver elements from the conduit and/or ambient conditions.

Optionally, in the sensor apparatus, the waveguide arrangement is fabricated from at least one of: a solid metal, from a composite material, from a sintered material.

Optionally, the sensor apparatus includes a plurality of the waveguide arrangements for interrogating a plurality of off-axis sectors of an interior volume of the conduit, wherein an extent of the off-axis sectors defines an annular region ("circle of construction") in which the sensor apparatus is operable selectively to measure the flow. More optionally, in the sensor apparatus, the off-axis sectors are determined in spatial extent by a steering direction and/or a frequency of modes which are excited in operation within the plurality of waveguide arrangements.

Optionally, the sensor apparatus further includes a data processing arrangement for providing driver signals to the transducer arrangement and for receiving signals from the transducer arrangement, wherein the data processing arrangement is operable to perform at least one of:

(a) at least one spatial measurement of one or more phases present within the conduit;

(b) at least one flow measurement of one or more phases present within the conduit;

(c) a spatial tomographic imaging of one or more sectors interrogated by the transducer arrangement;

(d) a Doppler flow measurement of inhomogenities, for example bubbles and/or sand particles, present within the conduit;

(e) a time-of-flight acoustic measurement through the one or more phases present in the conduit in operation, and along the wall of the conduit, in downstream and upstream flow directions, wherein the acoustic measurement along the wall of the conduit is used to provide error compensation for the acoustic measurement performed through the one or more phases;

(f) at least one measurement, wherein at least one of the transducer arrangements of a waveguide arrangement is operable both to send and to receive acoustic radiation to and from the conduit via use of pulse-echo interrogation of a flow within the conduit;

(g) a computation, based on time-of-flight measurements, of fluid flow rate within the conduit, and/or a fluid sound speed within the conduit;

(e) a computation to compensate for changing flow profiles and/or swirl occurring within the conduit;

(f) a computation to characterized a stratified flow occurring within the conduit;

(g) a measurement of structural integrity of the wall of the conduit, for determining at least one of: scale deposit, hydrate formation, wall thinning, embrittlement of the wall, micro-cracking within the wall of the conduit; and (h) a measurement of conduit diameter, for example for improving the calculation of volumetric flow rate According to a second aspect, there is provided a method of using a sensor apparatus to measure within a region of a conduit for guiding a flow, wherein the sensor apparatus includes a transducer arrangement disposed at least partially around an external surface of a wall of the conduit, characterized in that the method includes:

using one or more driver elements of the transducer arrangement for exciting in operation a helical acoustic wave propagation within the wall of the conduit for leaking acoustical energy from the helical acoustic wave propagation over an extensive area of the wall of the conduit for stimulating waves in chordal paths within the flow, wherein the waves in the choral paths within the flow re-enter the wall of the conduit to propagate further as a guided helical wave;

using one or more sensors of the transducer arrangement for receiving a re-entered portion of the acoustic wave propagation along the chordal paths within the flow which interacts with the flow and which includes information which characterizes properties of the flow; and operating the transducer arrangement to perform at least one of: switching between selected acoustic wave modes present in the acoustic wave propagation, steering an acoustic propagation direction of the acoustic wave propagation in a range lying between axial and radial directions relative to a central axis of the conduit.

Optionally, in the method, the acoustic propagation direction of the acoustic wave propagation includes axial and radial directions relative to a central axis of the conduit.

Optionally, the method includes using an elongate waveguide arrangement of the transducer arrangement for supporting a helical acoustic wave propagation therein from the one or more driver elements disposed at one or more ends of the waveguide arrangement.

Optionally, the method includes using an acoustic radiation damping arrangement of the waveguide arrangement for dampening back-and-forth acoustic wave propagation along the waveguide arrangement. More optionally, the method includes implementing the acoustic radiation damping arrangement by applying acoustic dampening material to the waveguide arrangement and/or by employing active damping of acoustic radiation.

Optionally, when implementing the method, the waveguide arrangement includes a waveguide having a rectangular cross-section. More optionally, when implementing the method, the waveguide arrangement has an aspect ratio in a range of 1:1 to 1:10.

Optionally, when implementing the method, the transducer arrangement includes one or more driver elements disposed in a phased array configuration, wherein the one or more driver elements are operable to provide steerable beams of acoustic radiation within an inner volume of the conduit when in operation.

Optionally, when implementing the method, the transducer arrangement includes a monitoring arrangement which is implemented using one or more additional sensors attached to the waveguide arrangement to measure acoustic wave propagation direction and/or amplitude within the waveguide arrangement.

Optionally, the method includes implementing the waveguide arrangement as a sheet, a collar, a helical elongate member, a helical strip, a structure formed integrally into the wall of the conduit.

Optionally, when implementing the method, the waveguide arrangement includes a waveguide for interfacing to the wall of the conduit, whose thickness and waveguide material are mutually substantially similar to a thickness and a material of the wall of the conduit.

Optionally, when implementing the method, the transducer arrangement includes one or more sensors which are implemented optically using one or more optical fibres, wherein one or more Bragg gratings are including along the one or more optical fibres for rendering the one or more optical fibres sensitive. More optionally, the method includes implementing the one or more optical fibres using at least one of: one or more fused silica monomode optical fibres, one or more sapphire monomode optical fibres.

Optionally, when implementing the method, the waveguide arrangement is detachable from the wall of the conduit.

Optionally, the method includes utilizing a thermal radiation shielding arrangement and/or an ionization shielding arrangement for the waveguide arrangement, for at least partially shielding the one or more driver elements from the conduit.

Optionally, when implementing the method, the waveguide arrangement is fabricated from at least one of: a solid metal, from a composite material, from a sintered material.

Optionally, the method includes implementing a contact between the waveguide arrangement and the conduit via a coupling material between associated abutting surfaces. More optionally, the method includes implementing the coupling material from at least one of: elastomer materials. a coupling cement, a coupling gel, a coupling adhesive.

Optionally, the method includes using a plurality of the waveguide arrangements of the sensor apparatus for interrogating a plurality of off-axis sectors of an interior volume of the conduit, wherein an extent of the off-axis sectors defines an annular region ("circle of construction") in which the sensor apparatus is operable selectively to measure the flow.

More optionally, when implementing the method, the off-axis sectors are determined in spatial extent by a steering direction and/or a frequency of modes which are excited in operation within the plurality of waveguide arrangements.

Optionally, the method includes using a data processing arrangement of the sensor apparatus for providing driver signals to the transducer arrangement and for receiving signals from the transducer arrangement, wherein the method further includes using the data processing arrangement to perform at least one of:

(a) at least one spatial measurement of one or more phases present within the conduit;

(b) at least one flow measurement of one or more phases present within the conduit;

(c) a spatial tomographic imaging of one or more sectors interrogated by the transducer arrangement;

(d) a Doppler flow measurement of bubbles present within the conduit;

(e) a time-of-flight acoustic measurement through the one or more phases present in the conduit in operation, and along the wall of the conduit, in downstream and upstream flow directions, wherein the acoustic measurement along the wall of the conduit is used to provide error compensation for the acoustic measurement performed through the one or more phases;

(f) at least one measurement, wherein at least one of the transducer arrangements of a waveguide arrangement is operable both to send and to receive acoustic radiation to and from the conduit via use of pulse-echo interrogation of a flow within the conduit;

(g) a computation, based on time-of-flight measurements, of fluid flow rate within the conduit, and/or a fluid sound speed within the conduit;

(e) a computation to compensate for changing flow profiles and/or swirl occurring within the conduit;

(f) a computation to characterized a stratified flow occurring within the conduit;

(g) a measurement of structural integrity of the wall of the conduit, for determining at least one of: scale deposit, hydrate formation, wall thinning, embrittlement of the wall, micro-cracking within the wall of the conduit; and (h) a measurement of conduit diameter, improving the calculation of volumetric flow rate According to a third aspect, there is provided a computer program product comprising a non-transitory computer-readable storage medium having computer-readable instructions stored thereon, the computer-readable instructions being executable by a computerized device comprising processing hardware to execute a method pursuant to the second aspect.

In another aspect, in the aforementioned sensor apparatus, the transducer arrangement includes a plurality of sets of waveguide transducers for generating and receiving the plurality of beams in cooperation with acoustic radiation propagation via the wall of the pipe, wherein the waveguide transducers include an elongate waveguide, and one or more transducer elements disposed at at least one end of the waveguide, and wherein a side portion of the waveguide is mounted in operation to an external surface of the wall of the pipe for coupling acoustic radiation to and from the wall of the pipe.

More optionally, in the apparatus, at least one waveguide of the transducer arrangement includes a first end thereof and a second end thereof, wherein an array of transducer elements is disposed at the first end and are individually excitable in a phase-array manner for steering the one or more beams within the region, and the one or more transducer elements are disposed at the second end for monitoring integrity of operation of the waveguide and/or for enabling a temperature compensation to be applied by the signal processing arrangement for operation of the waveguide.

Optionally, in the apparatus, the transducer arrangement includes a spatially distributed array of sensors disposed on an external surface of the wall of the pipe for receiving acoustic radiation coupled through the wall of the pipe thereto.

More optionally, in the apparatus, the spatially distributed array of sensors is implemented using a plurality of Bragg grating filter sensors distributed along one or more optical fibres, wherein the Bragg filter sensors are optically interrogated in operation via optical radiation guided through the one or more optical fibres and selectively reflected and/or transmitted at the Bragg grating filter sensors (FBG).

More optionally, in the apparatus, the spatially distributed array of sensors is interspersed between waveguides of the transducer arrangement for detecting spatial variation in flow characteristics, as sensed by the plurality of beams, for example propagating along chordal paths.

Optionally, in the sensor apparatus, the one or more elements are operable to utilize broadband signals, which are efficiently transmitted to the wall of the structure as the transducer waveguide has a similar dispersion characteristic as the wall of the structure.

It will be appreciated that features of the invention are susceptible to being combined in various combinations without departing from the scope of the invention as defined by the appended claims.

DESCRIPTION OF THE DIAGRAMS

Embodiments of the present invention will now be described, by way of example only, with reference to the following diagrams wherein.

Figure 3:
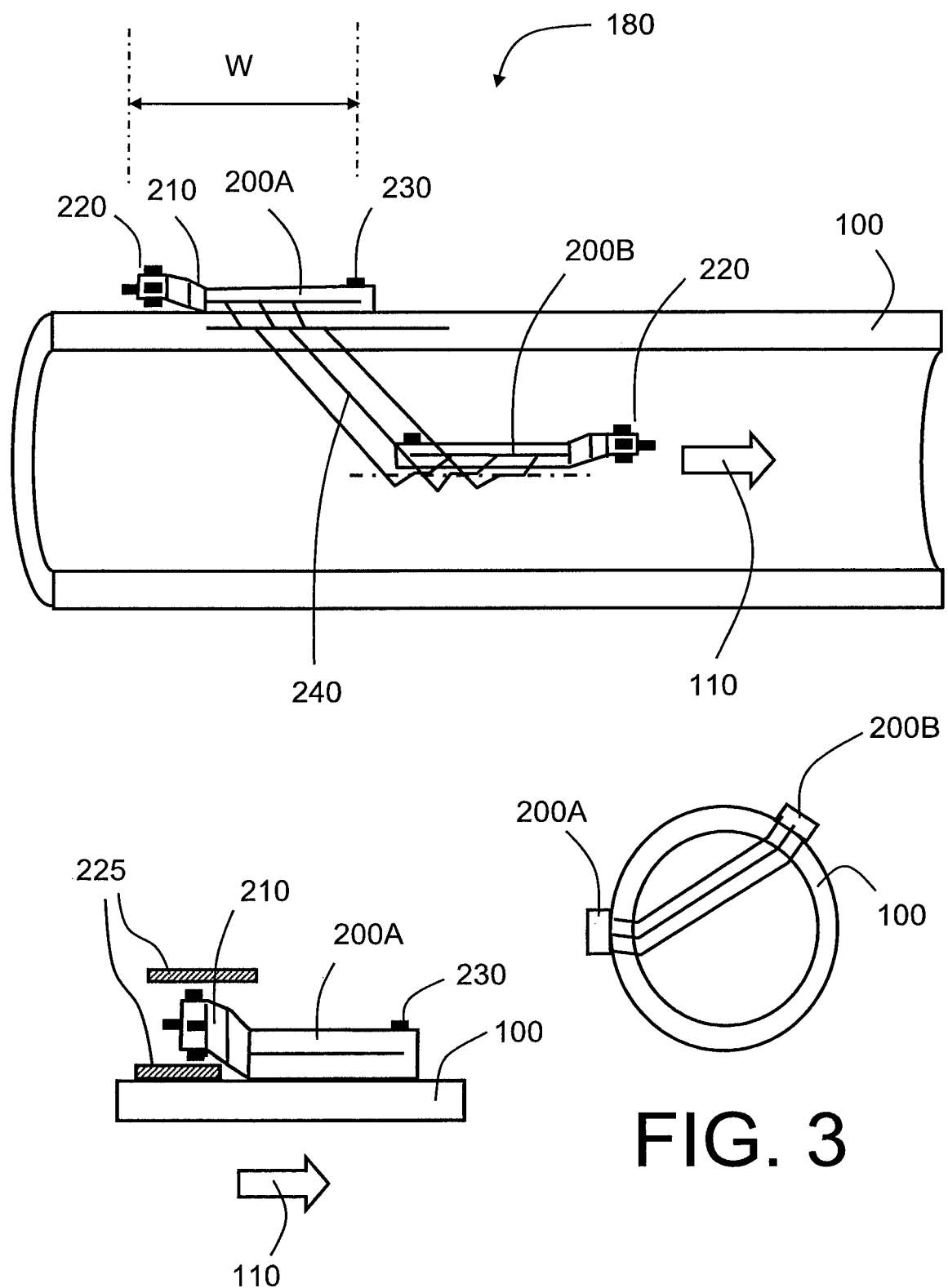
FIG. 3 is a schematic illustration of a transducer arrangement employed in an apparatus for measuring flow rate within a conduit, pursuant to the present disclosure, wherein the transducer arrangement is illustrated in symbolic form but is beneficially implemented in a helical manner in practice.
Figure 4:
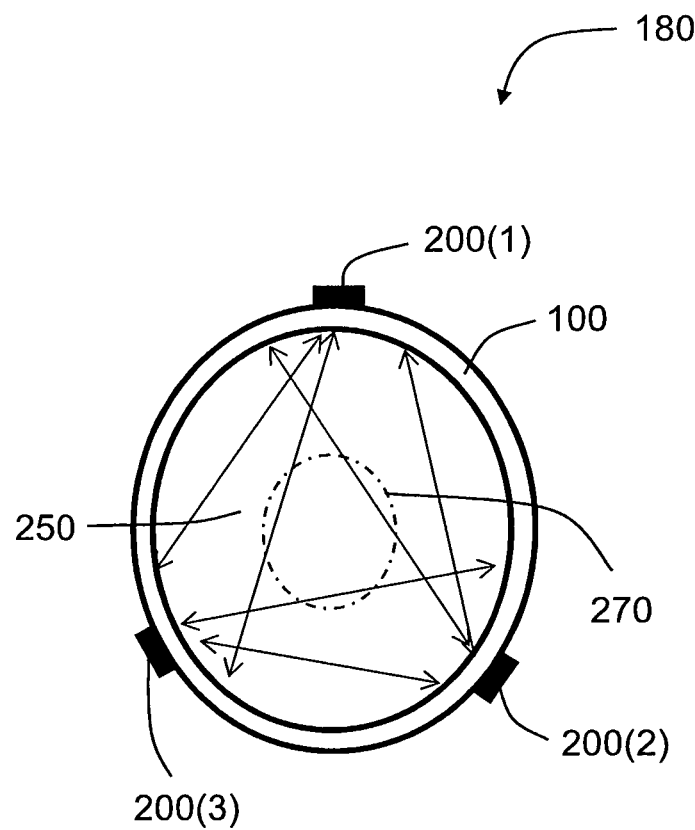
Figure 5:
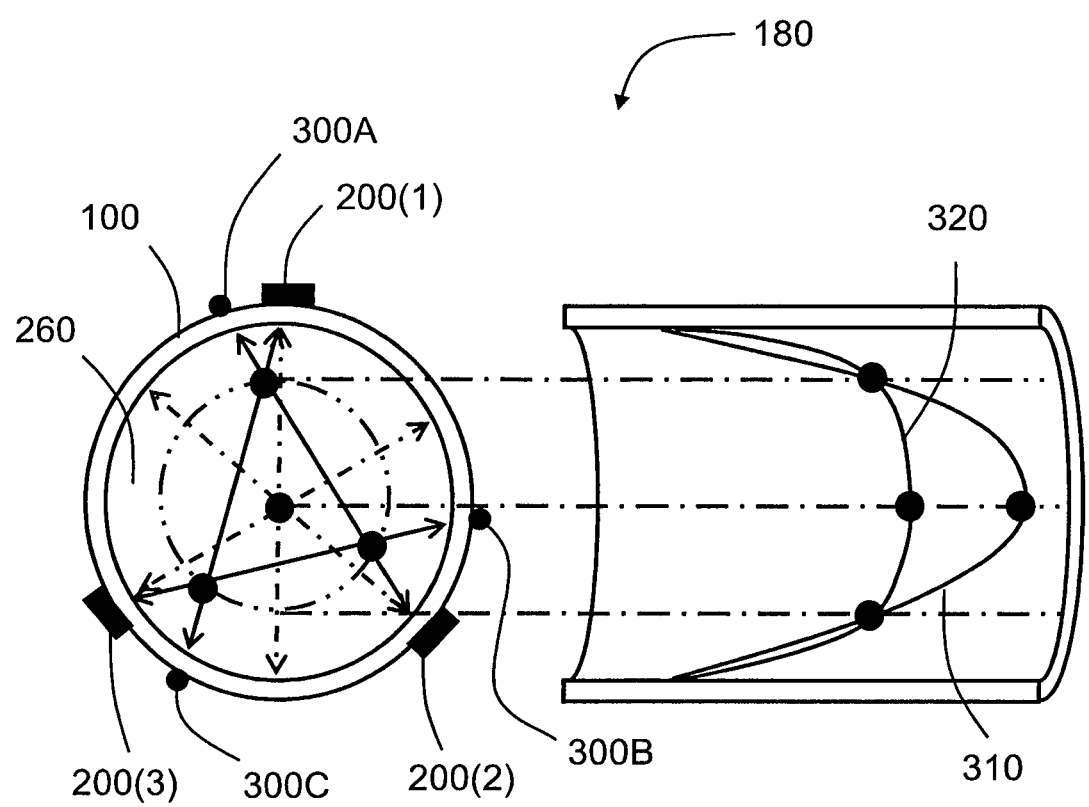
Figure 6:
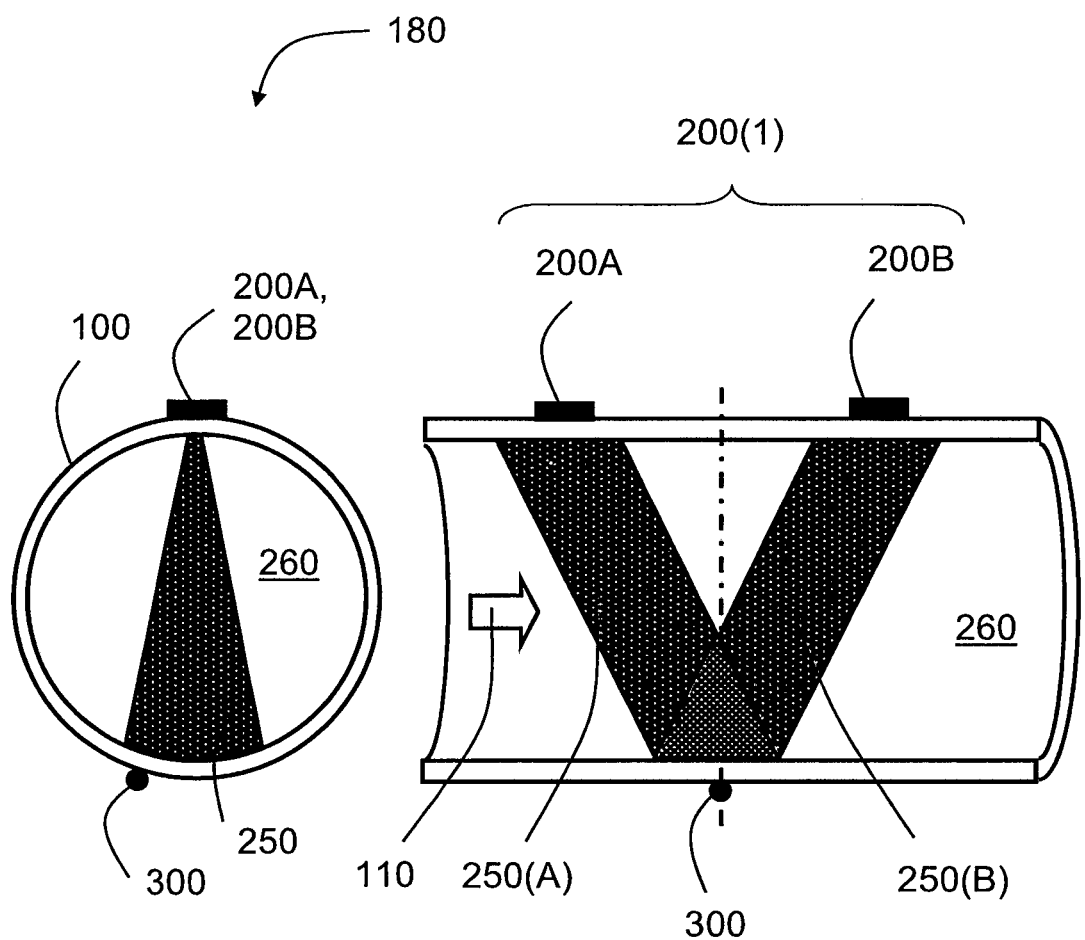
Figure 7:
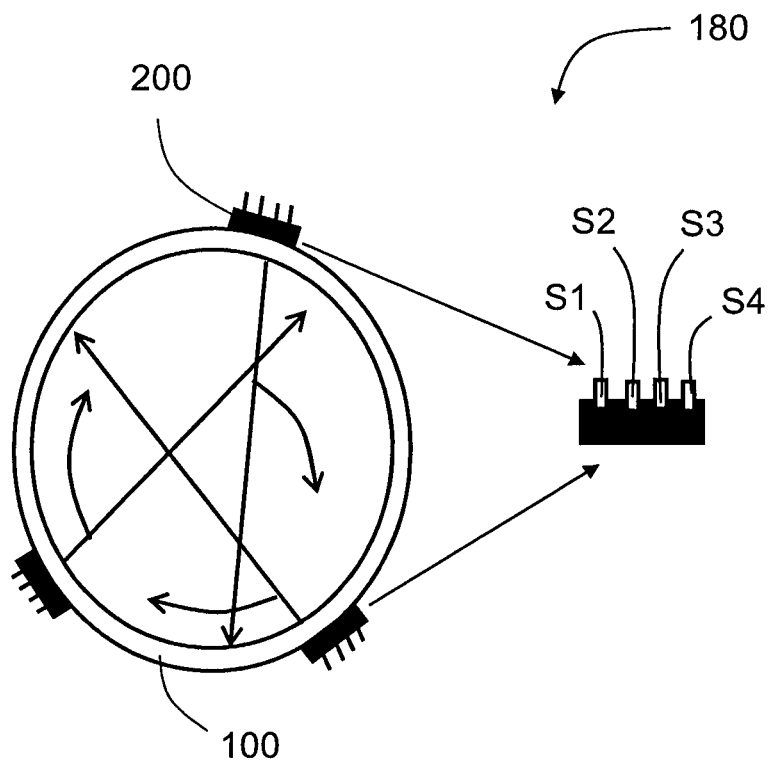
Figure 7:
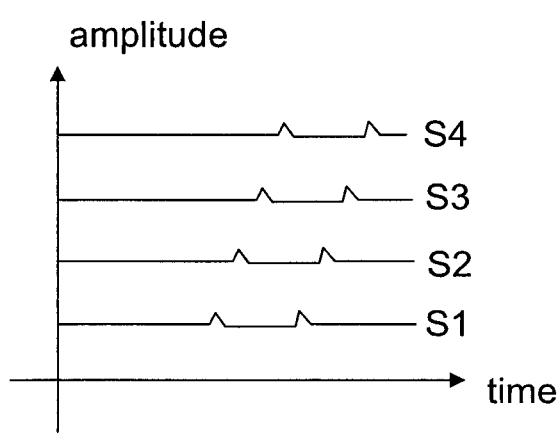
Figure 8:
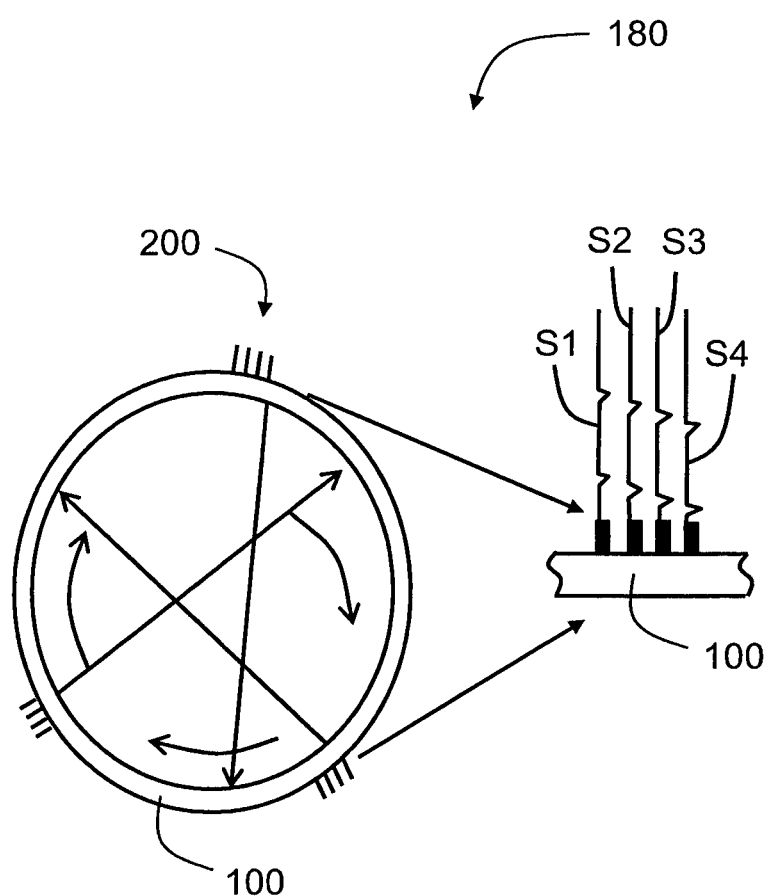
Figure 9:
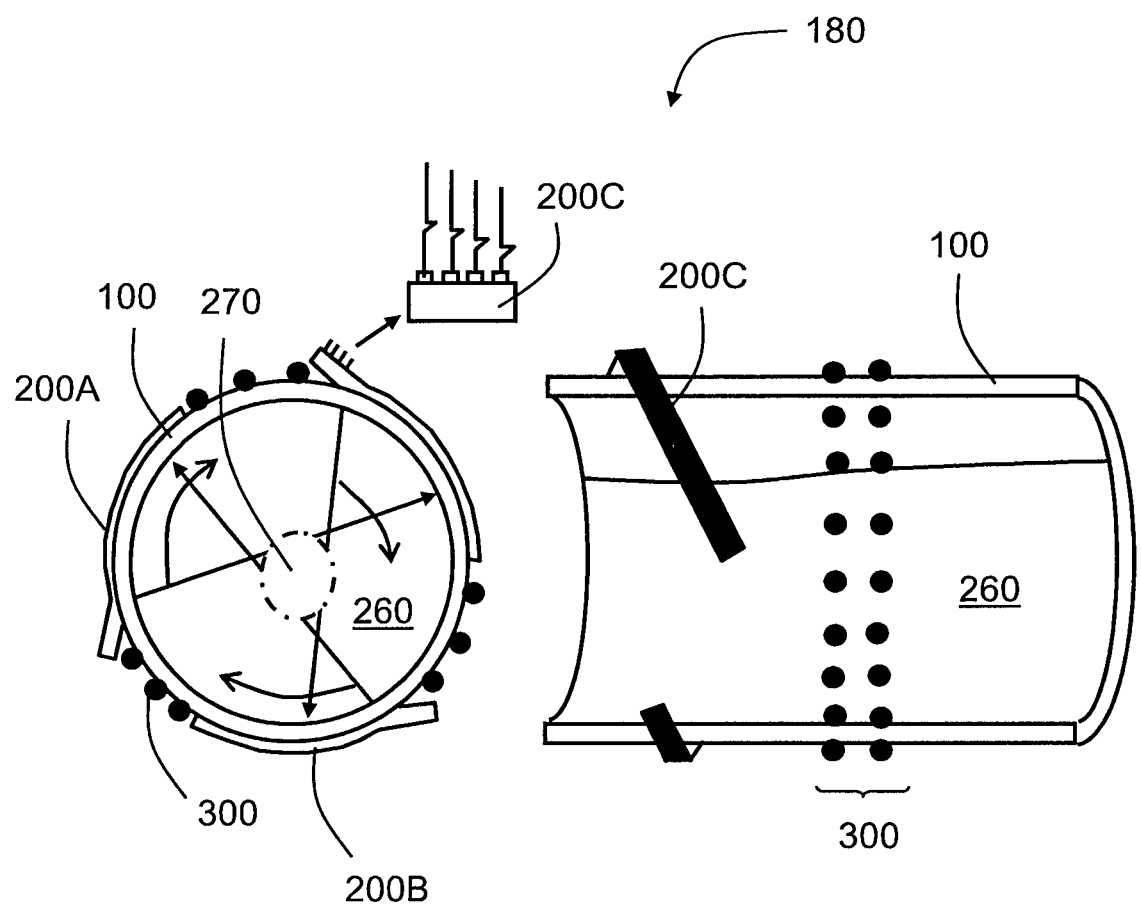
Figure 10:
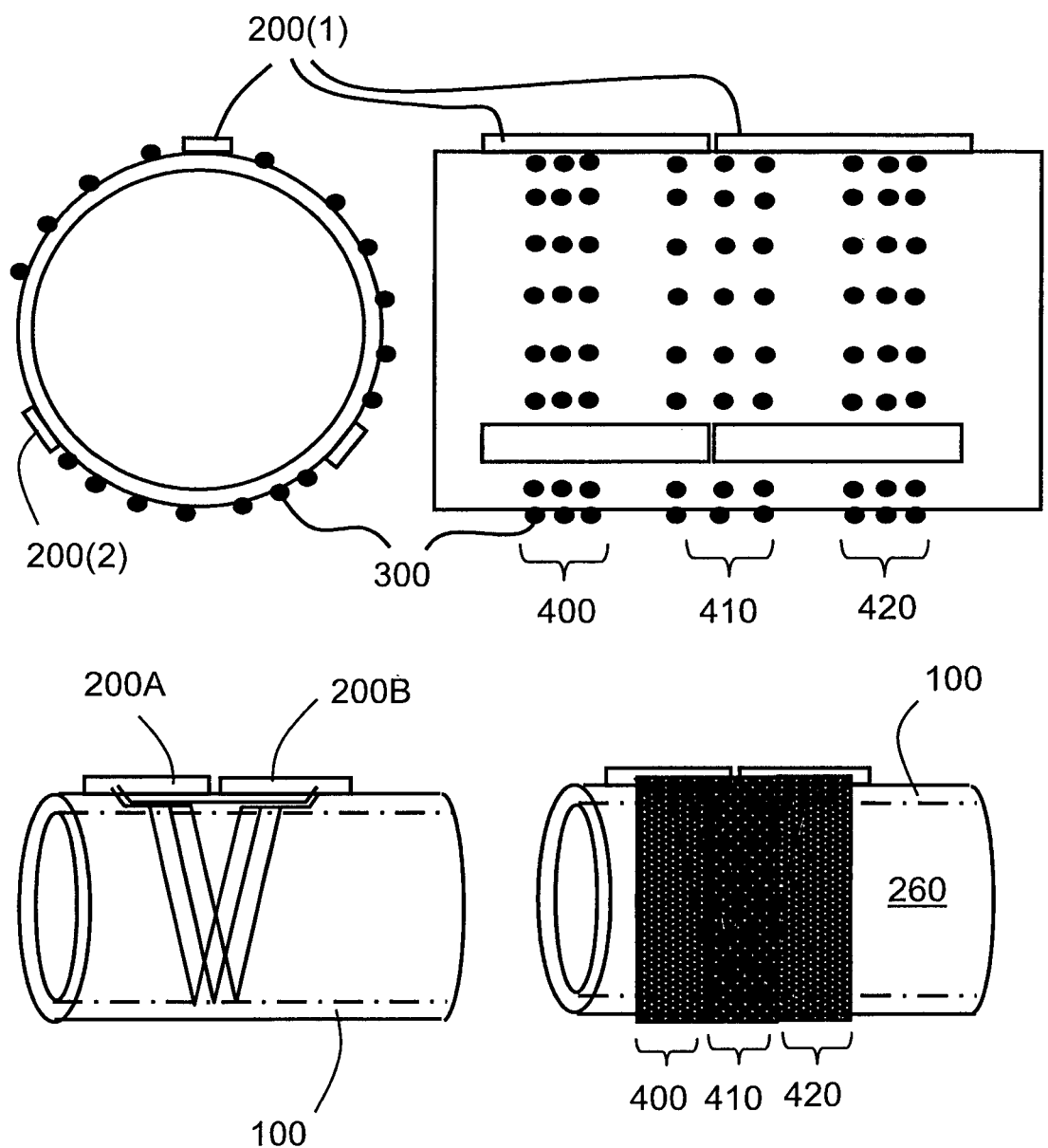
Figure 11:
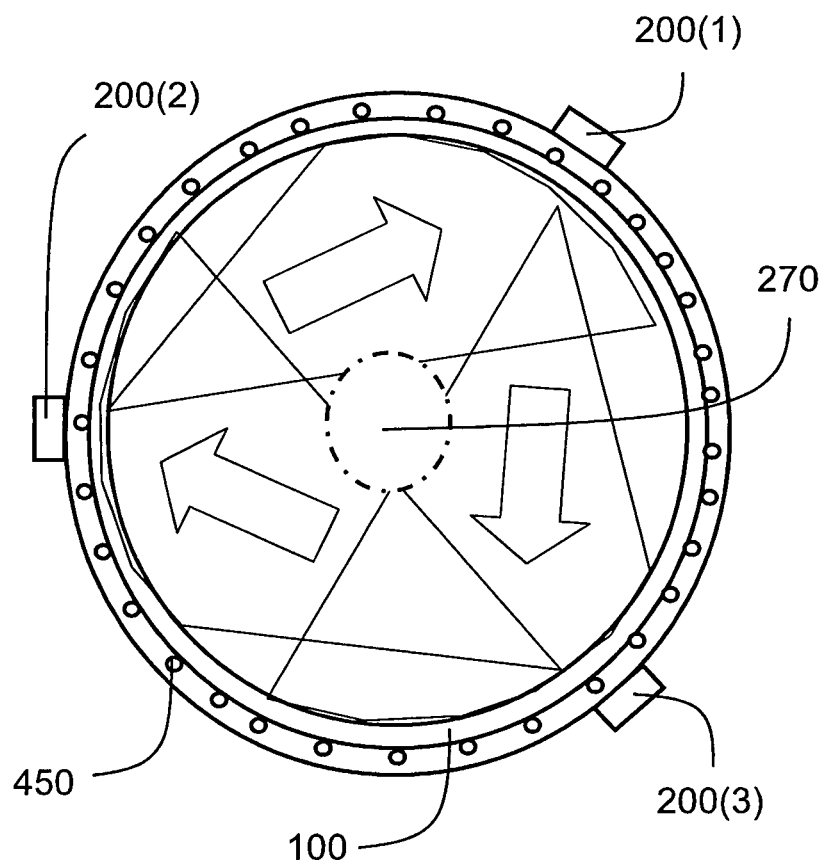
Figure 12:
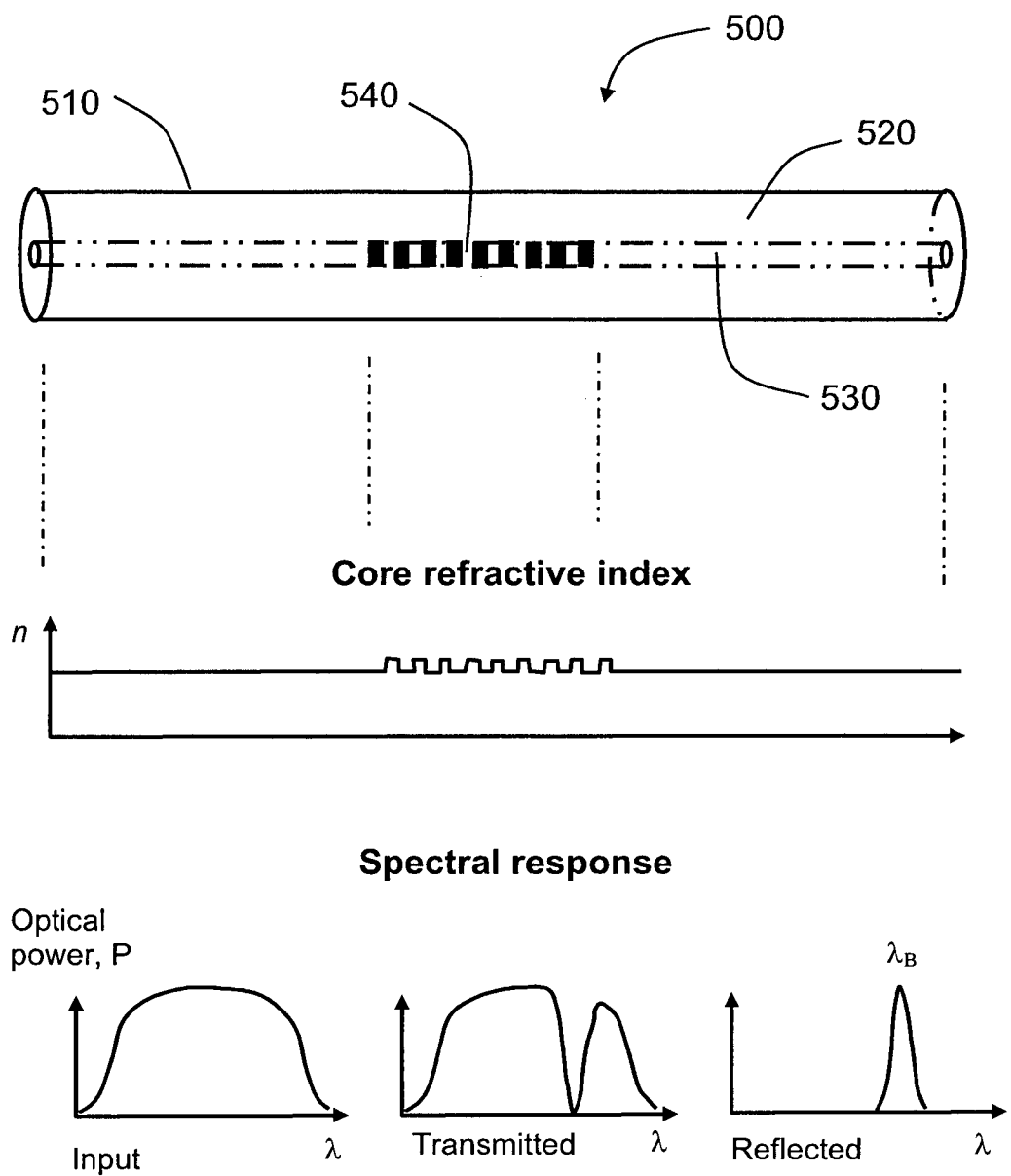
Figure 13:
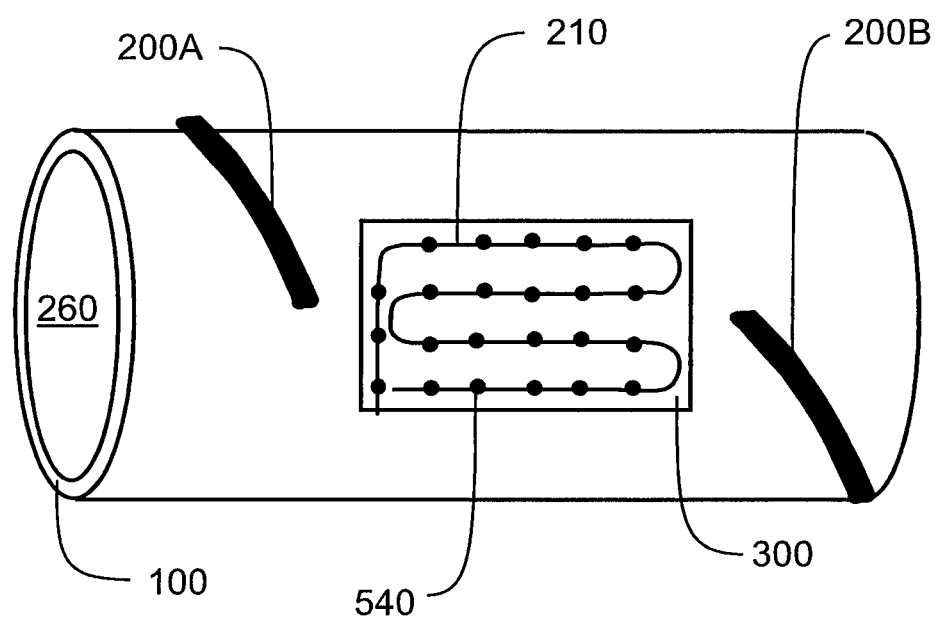
Figure 14:
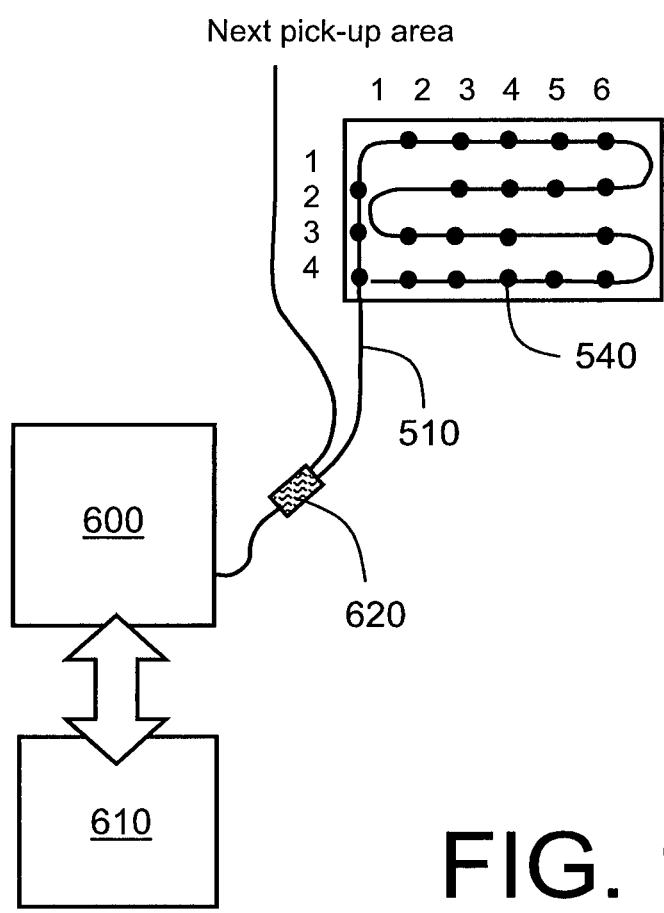
Figure 15:
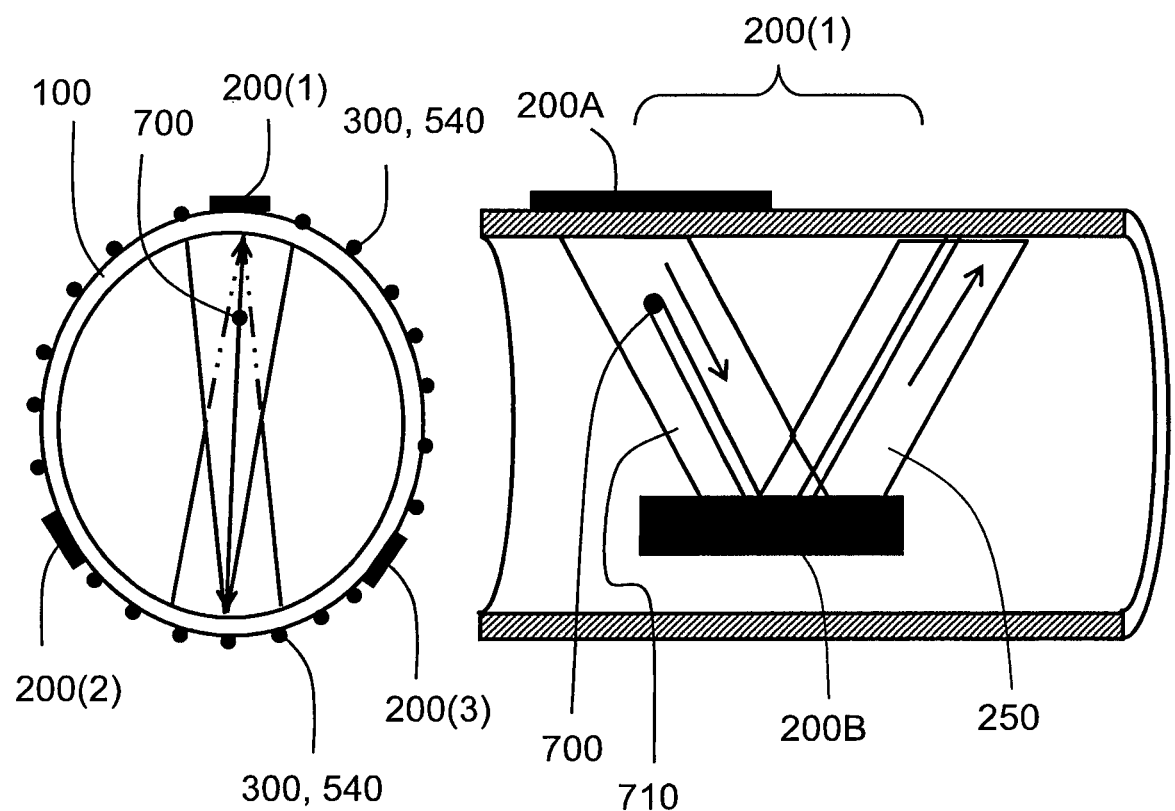
Figure 16:
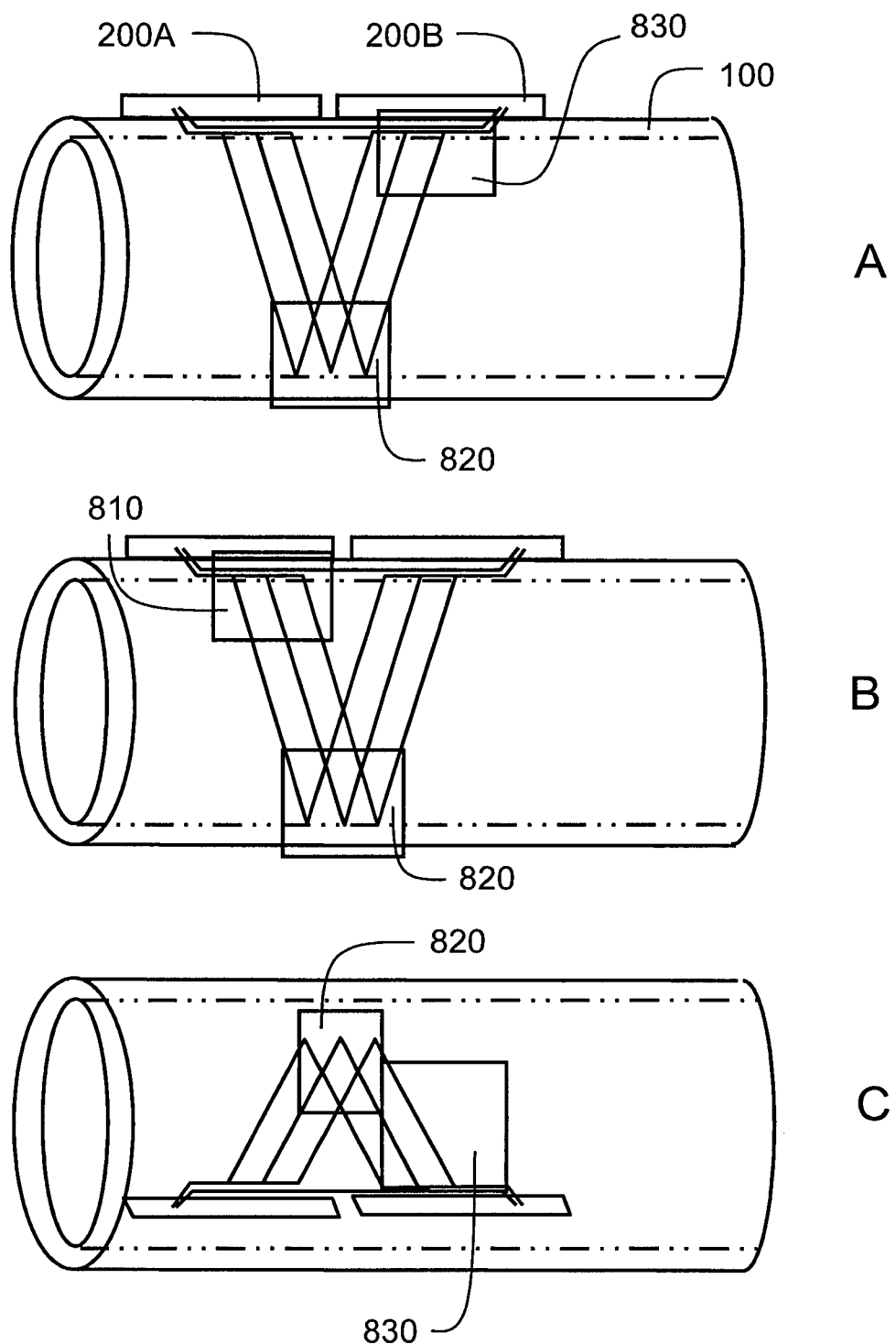
Figure 17:
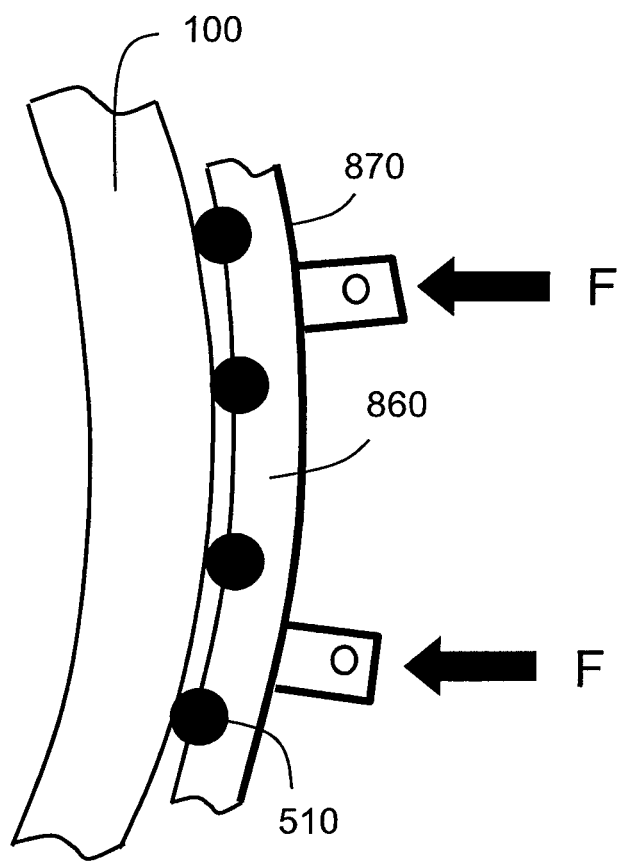

FIG. 4 is a schematic cross-section illustration of the conduit of FIG. 3, wherein a radial disposition of transducers for measuring flow rate is shown, together interrogated by chordal paths ("chordal paths") of acoustic radiation propagation for interrogating corresponding sectors of a cross-section of the a conduit, together with a illustrative representation of a "circle of construction" bounded by the sectors;

FIG. 5 is an illustration of the conduit of FIG. 4, wherein a measurement method is shown for measuring flow velocity at a central-axis position and at a plurality of off-axis positions, for example at three off-axis positions, for a laminar flow condition and also for a situation approaching an onset of turbulence;

FIG. 6 is an illustration of the conduit of FIG. 3, wherein upstream and downstream measurement positions are shown;

FIG. 7 is an illustration of a manner in which off-axis interrogating beams of ultrasonic radiation are generated by employing phase-array ultrasonic transducers excited by mutually phase-shifted and/or time delayed excitation signals S1 to S4;

FIG. 8 is an illustration of an alternative manner in which off-axis interrogating beams of ultrasonic radiation are generated by employing phase-array ultrasonic transducers excited by mutually phase-shifted and/or time delayed excitation signals S1 to S4;

FIG. 9 is an illustration of a manner in which emitting transducers and receiving transducers are disposed around the conduit of FIG. 3;

FIG. 10 is an illustration of an optional alternative manner in which emitting transducers and receiving transducers are disposed around the conduit of FIG. 3; optionally, the emitting transducers are disposed in a helical manner around the conduit;

FIG. 11 is an illustration of measuring fields of the transducers and their associated receiving transducers of FIG. 9 and FIG. 10, wherein the transducers are implemented in a helical manner for exciting helical acoustic radiation in the wall of the conduit;

FIG. 12 is an illustration of a Bragg-grating optical sensor which is employable for implementing the receiving transducers of FIG. 9 and FIG. 10;

FIG. 13 is an illustration of an arrangement for emitting transducers and receiving transducers for measuring flow within the conduit of FIG. 3;

FIG. 14 is an illustration of an optical-fibre connection and data processing arrangement for use with the receiving transducers shown in FIG. 9 to FIG. 13;

FIG. 15 is an illustration of ultrasonic radiation propagation paths within the conduit or pipe of FIG. 3, in a presence of a particle within the conduit; the transducers are illustrated in a linear format, although are beneficially implemented in a helical format;

FIG. 16 is an illustration of different sensing strategies employable within apparatus pursuant to the present disclosure;

FIG. 17 is an illustration of a manner in which receiving transducers are mounted to the conduit or pipe of FIG. 3; and FIG. 18 to FIG. 27 are illustrations of a spatial implementation of a helical waveguide transducer pursuant to the present disclosure.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

In the following description, a conduit is to be construed to relate to spatial structure, for example a pipe, which is operable to confine and guide a flow of a fluid therethrough. The conduit is optionally, for example, a pipeline, a pipe, a vessel or similar. Although a conduit is illustrated in the diagrams as having a circular cross-section, it will be appreciated that other type of cross-sections are feasible, for example a rectangular cross-section.

In overview, an apparatus 180 pursuant to the present disclosure beneficially employs "CMR Guided Wave" technology as described in Norwegian patent NO331687 and corresponding GB patent GB2479115B, PCT patent application WO2011/078691A2 and U.S. Pat. No. 8,141,434B2, which are hereby incorporated by reference. Moreover, the apparatus 180 pursuant to the present disclosure includes additional features:

(i) acoustic emitting transducers, for example ultrasonic guided wave transducers, employed in the apparatus 180 are elongate and include an acoustic waveguide which is coupled to an external surface of a conduit in which flow is to be measured. Moreover, such an approach enables the apparatus 180 to achieve more accurately acoustic mode selection and suppression, thereby increasing measurement accuracy and reliability. Furthermore, such an approach is capable of reducing effects of temperature changes compared to known wedge-shaped acoustic coupling element technology, which provide substantially a point coupling of acoustic radiation to and from the conduit, and is also capable of providing for single or multiple piezo-element positions along geometrical x-, y- and z-axes, as will be described in more detail later in this disclosure;

(ii) "Off-centre beam": the apparatus pursuant to the present disclosure employs non-intrusive ultrasonic guided wave transmission, wherein an acoustic beam excitation is employed at an angle which propagates outside a central region of the cross-section of the conduit of FIG. 3, namely via off-axis chordal paths within the conduit; and (iii) "Spatial detector grid": an array of acoustic receiving sensors which are disposed in a grid-like manner around an external surface of the conduit of FIG. 3, wherein the spatial detector grid enables multiple point velocity and attenuation measurements to be performed in operation across a fluid cross-section of the conduit of FIG. 3, thereby enabling fluid dynamic monitoring to be performed in cross-section slices or as a cross-section "3D volume". Such measurement enables spatially inhomogeneous complex mixtures within the conduit of FIG. 3 to be characterized, by way of a form of tomography, for example eventually multiphase flows.

There is thereby achieved a non-invasive flow meter capable of providing more accurate flow rate measurements for any combination of oil, water and gas, as well as providing flow measurement conforming to very low measurement uncertainty, resulting in accuracy compliant to national and international regulations for fiscal transfer of liquid and gas, including oil and gas allocation, which include measurement of gas containing liquid and liquid containing gas.

In the following description, the term "acoustic" is to be construed broadly to include any acoustic signals, for example aforesaid ultrasonic radiation, for example to acoustic signals having a frequency in a range of 100 Hz to 1 MHz, and more optionally in a range of 10 kHz to 1 MHz. Optionally, the sensor apparatus 180 is operable in a passive listening mode, wherein signals received at the Bragg-filter-grating sensors 500 are of use in characterizing the flow 110, in addition to interrogating the flow 110 by injecting acoustic radiation therein, as described in the foregoing. Optionally, neural network analysis of passively-received acoustic signals from the flow 110 is used to obtain confirmation and/or additional information which assists to characterize the flow 110.

The apparatus pursuant to the present disclosure is beneficially operable to employ following measurement regimes:

(i) an acoustic beam interrogation for monitoring gas in a liquid flow within the conduit of FIG. 3;
(ii) an acoustic beam interrogation for monitoring liquid in a gas flow within conduit of FIG. 3;
(iii) an acoustic beam interrogation in combination with a liquid flow velocity based liquid fraction computation, for monitoring water in oil flow within conduit of FIG. 3; and
(iv) an acoustic beam interrogation in combination with a liquid flow velocity based liquid fraction computation, for monitoring oil in water flow within conduit of FIG. 3.

Figure 1:
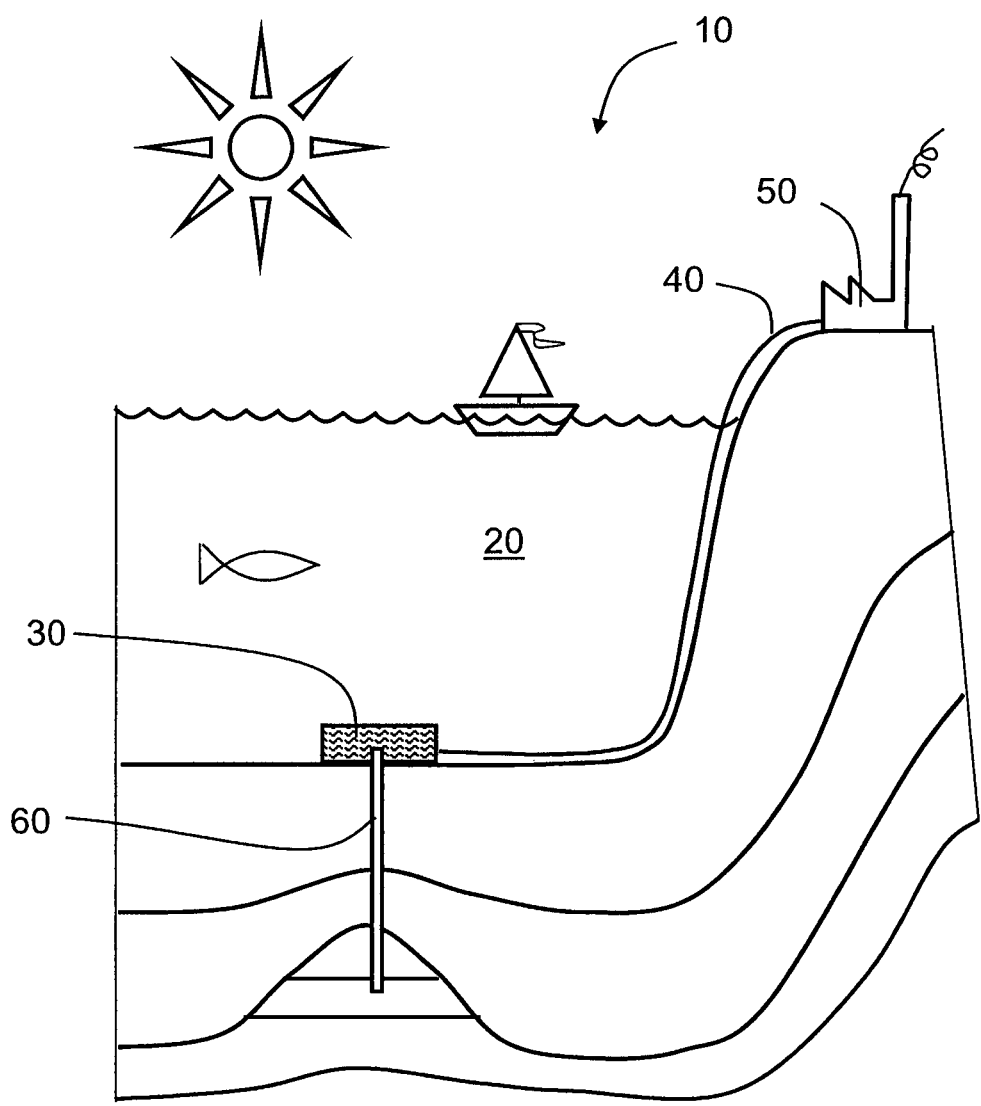
FIG. 1 is an illustration of an off-shore environment in which characteristics of a multiphase flow are to be measured.
Figure 2:
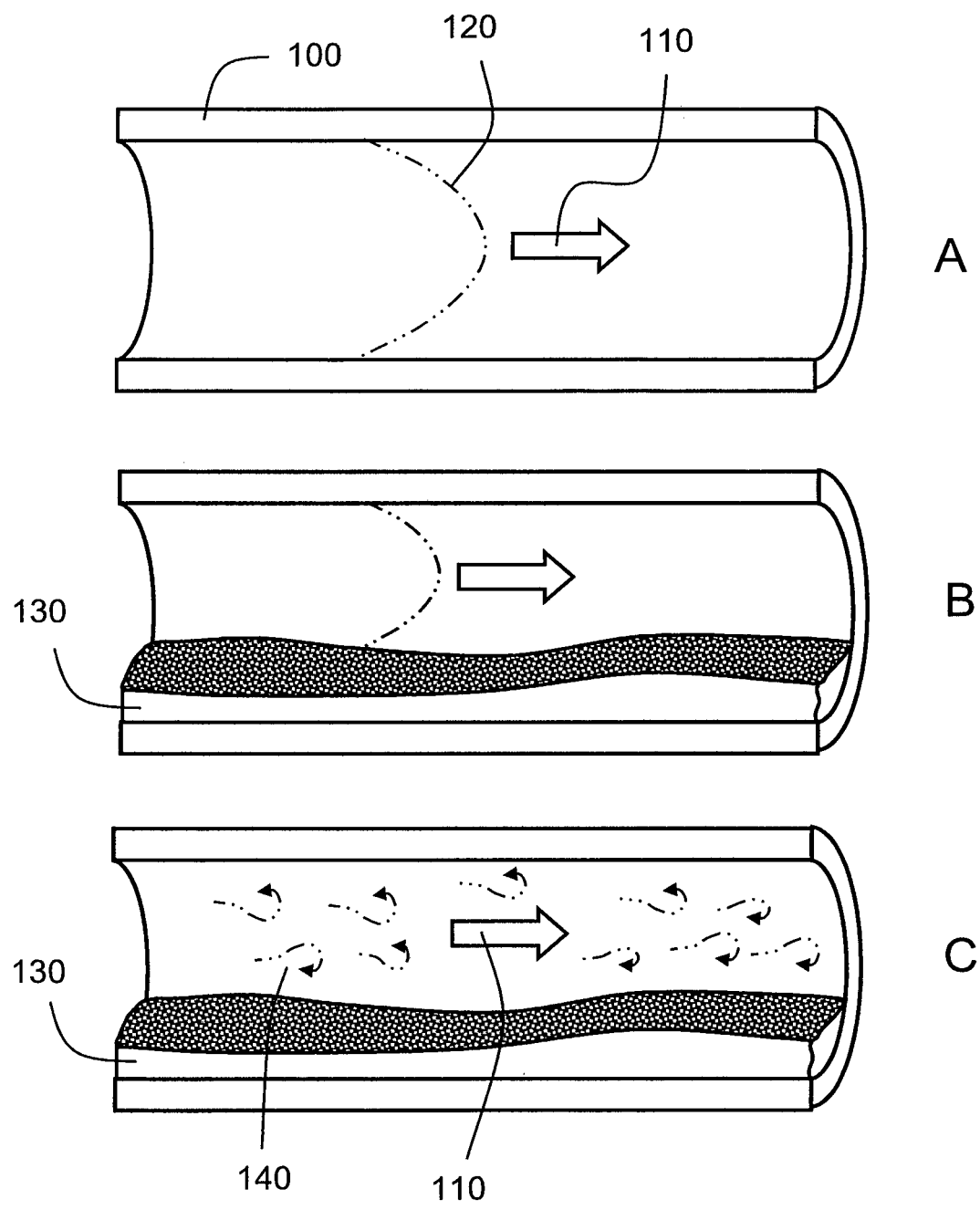
FIG. 2 is a schematic illustration of spatially inhomogeneous complex flows within a conduit.

Referring next to FIG. 2, there is shown example of a flow, denoted by an arrow 110, through a conduit denoted by 100; as aforementioned, the conduit 100 is a pipe, for example. In a situation A, the flow 110 is laminar, namely non-turbulent, wherein a spatial velocity of the flow 110 decreases as a function of a radial distance from a central elongate axis of the conduit 100. It will be appreciated from the situation A that a single flow measurement for the conduit 100 corresponds to a form of aggregate of spatial flow velocities in various spatial regions of the conduit 100. For example, a lower flow velocity occurring locally at an inside surface of a wall of the conduit 100 can, for example, give rise to deposition, for example formation of scale on the inside surface, over a prolonged period of operation. The flow 110 can be a complex flow, for example a spatially substantially homogeneous flow, or a spatially inhomogeneous flow as illustrated in situation B, wherein a spatial region 130 has a different composition to a remainder of the flow 110 within the conduit 100. However, when the flow 110 exceeds its Reynolds number $R_e$, see Equation 1 (Eq. 1) below, turbulent flow occurs, resulting potentially in vortices 140 and other instabilities, wherein a broadened spectrum of flow velocities within the conduit 100 then occurs. It will be appreciated, especially in the situation C, that a single aggregate flow measurement for the conduit 100 is insufficient to describe complexities of the flow 110 occurring with the conduit 100. The present disclosure describes the apparatus 180 which is both capable of providing a very accurate measurement of the flow 110 in situation A, for example within national and international fiscal metering regulation requirements, as well as being able to cope with providing a set of measurements of the flow 110 in the situation C. The apparatus 180 achieves such accurate measurement by acquiring a series of acoustic measurements, for example ultrasonic measurements, in various operating configurations of the apparatus 180, and then applying various analytical computations to the series of acoustic measurements, as will be described in greater detail later in this disclosure. The analytical computations are beneficially implemented using computing hardware, for example using an array of high-speed RISC processors ("Reduced Instruction Set Computer") which are especially efficient at handling matrix computation required for performing tomographic imaging of regions of the conduit 100. Beneficially, the computations implement algorithms that are encoded into one or more software products recorded on machine-readable data storage media.

Referring next to FIG. 3, there is shown an apparatus 180 including an arrangement of transducers for implementing an instrument pursuant to the present disclosure. The arrangement of transducers includes a first transducer including an elongate waveguide 200A having a length W measuring from a cluster of acoustic elements 220 disposed at a first end of the waveguide 200A, via a coupling neck region 210, to a monitoring element 230 disposed at a second end of the waveguide 200A. The arrangement of transducers further includes a second elongate waveguide 200B disposed in a mirror orientation to the first elongate waveguide 200B, in a manner as illustrated. Sides of the waveguide 200A, 200B are attached to an external surface of the wall of the conduit 100 for coupling acoustic radiation into the wall of the conduit 100 and therefrom to an interior region of the conduit 100 in which the flow 110 occurs in operation; such coupling occurs over an extensive area along the waveguides 200A, 200B in comparison to known ultrasonic transducers, for example wedge-type transducers, EMAT transducers, comb-type transducers and similar, which couple their acoustic energy over a relatively small area corresponding substantially to a point coupling. The coupled acoustic radiation is denoted by 240.

In operation, measurements are optionally made with the acoustic radiation 240 projected in upstream and downstream directions relative to the flow 110, and a differential computation is performed thereby removing many sources of measurement error in the apparatus 180.

Optionally, these measurements include measurements of acoustic radiation propagation in upstream and downstream directions through the flow 110, and also acoustic radiation propagation in upstream and downstream directions through the wall of the conduit 100, thereby providing four different measurements, for example four time-of-flight pulse measurements. By applying the four time-of-flight pulse measurements to an algorithm, various transducer errors can be substantially eliminated from flow computations for determining a flow velocity of the flow 110. The two measurements through the wall of conduit 100 provide information for correcting various errors occurring in the two measurements made through the flow 110.

The monitoring elements 230 are beneficially employed to monitor acoustic radiation coupled from the cluster of acoustic elements 220 to the waveguide 200A, thereby enabling correction of element characteristics to be compensated, for example changes in piezo-electric coupling coefficient of the elements of the cluster as a function of operating temperature and/or time; these acoustic elements are beneficially mounted at an face of a distal end of the waveguide 200A as illustrated, and further elements mounted on a plurality of sides of the distal end of the waveguide 200A, as illustrated in FIG. 3. Such a configuration enables the waveguide 200A to have selectively excited therein Lamb waves, shear waves and Rayleigh waves. For example, the piezo-electric elements have a coupling coefficient which slowly reduces as a function of time, for example as a result of piezo-electric element depolarization. Alternatively, in another embodiment the differential computation is performed on received phase shifted, namely Doppler shifted, acoustic radiation. Similarly, the speed of sound may optionally be used for WLR, which combined with the attenuation measurements will give a multiphase measurement. As an example, such an approach is beneficial to employ when the flow 110 includes a high degree of inhomogeneity, for example numerous bubbles, which cause gross attenuation of acoustic radiation which is otherwise capable of propagating along off-axis chordal paths through the flow 110.

The elongate waveguides 200A, 200B provide transducers which are superior to commonly-used acoustic transducers employing wedge-shaped acoustic coupling elements; such known wedge-shaped acoustic coupling elements are operable to excite shear-wave acoustic beams within the conduit 100, whereas the elongate waveguides 200A, 200B are capable of selectively exciting shear waves as well as other forms of acoustic waves, for example various orders of Lamb waves, as well as high-frequency Rayleigh waves, as aforementioned. Such superiority pertains, for example, to improved guided wave properties and better beam formation of the acoustic radiation 240, for example ultrasonic radiation. Thus, the elongate waveguides 200A, 200B are operable to provide improved directing and shaping of selected acoustic mode transmission within the conduit 100, for example for optimal utilization of transmitted acoustic radiation. Moreover, the elongate waveguides 200A, 200B are operable to provide improved suppression of acoustic modes which have not been selected for use in the apparatus 180, thereby enhancing measurement signal-to-noise ratio of the apparatus 180. Furthermore, in comparison to known wedge-coupling-element technology, the elongate waveguides 200A, 200B additionally results in less signal drift caused by thermal wedge material expansion and contraction, as well as increased transducer foot-print area onto the external surface of the conduit 100, namely more acoustic radiation coupled into the conduit 100. Additionally, the waveguides 200A, 200B have an extended physical length, in comparison to known wedge-design transducers, which enables additional acoustic pickup, for performing following functions:

(i) acoustic energy is coupled into a sensing direction of a correspondingly shaped receiving transducer, thereby improving measurement signal-to-noise performance of the apparatus 180; and (ii) acoustic energy is focused in a direction and shape of a receiving array of sensors, for example Bragg-grating sensors, as will be described in greater detail later The coupling neck region 210 is also an advantage, because shielding 225 is optionally inserted to protect the cluster of acoustic elements 220 from an external surface of the conduit 100 and/or from an environment surrounding the conduit 100. Such shielding 225 includes, for example, one or more thermal insulation layers and/or one or more ionizing radiation protection layers. The one or more thermal insulation layers optionally include one or more layers of conductive reflective material as well as mineral-based insulation therebetween. The one or more ionizing radiation protection layers are optionally fabricated from materials such as lead, bismuth, boron-containing materials or similar. Moreover, such shielding 225 beneficially protects the cluster of acoustic elements 220 from radiation which otherwise could potentially cause ageing of piezoelectric materials of the acoustic elements 220, namely causing dislocations and de-polarization thereof.

Spatial free ends of the waveguides 200A, 200B are provided with the monitoring elements 230 which are beneficially employed in a feedback manner to control drive signals to the cluster of acoustic elements 220 to optimize their operation, for example:

(i) for optimizing acoustic mode propagation within the waveguides 200A, 200B for selectively controlling a direction of propagation of corresponding acoustic modes within the wall of the conduit 100, and thereby, for example, a spatial extent and/or direction of corresponding acoustic wave propagation within an inner volume of the conduit 100; by such an approach, selectable radial "construction circles", denoted by 270 in FIG. 4, are feasible to define for each sector of the conduit 100 addressed by the waveguides 200A, 200B, for example for performing real-time tomographic spatial analysis of multiphase flows occurring within the conduit 100 in operation; and (ii) for achieving an enhanced measurement signal-to-noise ratio.

It will be appreciated that for a given angle of the helical Lamb-wave acoustic propagation within the wall of the conduit 100, there is a corresponding "circle of construction" 270. Thus, by varying the angle of the of the helical Lamb-wave acoustic propagation within the wall of the conduit 100, a different diameter "circle of construction" 270. is obtained in the sensor apparatus 180. The angle of the of the helical Lamb-wave acoustic propagation within the wall of the conduit 100 is selected in the sensor apparatus 180 by selecting a given frequency for the Lamb-wave propagation and/or by employing beam steering methods when the waveguide 200 is constructed to allow for such beam steering to occur.

Optionally, the cluster of elements 220 are installed in a same plane or at different angles along x-, y- and z-axes, and controlled individually with respect of signal wave phase, namely in a manner of a phased array:
(i) for achieving an optimal operating signal-to-noise ratio;
(ii) for controlling acoustic transmission angle excitation in respect of the conduit 100 and one or more phases flowing within the conduit 100; and
(iii) for achieving sequential transmission angles for the acoustic radiation 240, as well as signal shape and/or signal quality for exciting various types of signals on demand, for example a given number of pulses X in a first given transmission angle for the radiation 240, followed by a given number of pulses Y in a second given transmission angle for the radiation 240, then returning to the given number of pulses X in the first given transmission angle, and so forth; there is thereby obtained two sets of measurements representing mutually different fluid properties by employing only one set of transducers, as illustrated in FIG. 3 and FIG. 4.

In FIG. 3, at least one transducer of the cluster of transducers 220 is mounted at a distal end face of the waveguide 200; this at least one transducer is optionally excited alone for causing shear waves to propagate along the waveguide 200 to be coupled into the wall of the conduit 100. Moreover, at least one transducer of the cluster of transducers 220 is mounted to a side face of the distal end of the waveguide 200; this at least one transducer is optionally excited alone for causing Rayleigh waves to propagate along the waveguide 200 to be coupled into the wall of the conduit 100. Beneficially, a plurality of sides of the distal end of the waveguide 200 are provided with corresponding transducers, for example as illustrated on three sides of the distal end. By selectively exciting one or more of the transducers in combination, various acoustic propagation modes are selectively excited within the waveguide 200, for example for exciting in the wall of the conduit 100 at least one of: shear waves, Lamb waves, Rayleigh waves, but not limited thereto. Beneficially, the Lamb waves that are coupled in operation to and from the wall of the conduit 100 follow a helical path and optionally couple to a region within the conduit 100 over an extensive area of the wall of the conduit 100; in contradistinction, shear waves are customarily coupled to an interior of a conduit over a relative small area, corresponding substantially to a point location of ultrasonic radiation injection in the interior of the conduit 100.

Optionally, the waveguide 200 is fabricated so that a cluster of transducers 220 is disposed at each end of the waveguide 200, so that excitation of specific selected modes within the waveguide can be monitored in operation. When the cluster of transducers 220 at a first distal end of the waveguide 200 are implemented using piezo-electric elements, and the cluster of transducers 220 at a second distal end of the waveguide are implemented as an array of Bragg-grating sensors, a feedback arrangement is beneficially employed to control an amplitude and/or direction of acoustic radiation propagating within the waveguide 200, for example to correct of non-deterministic ageing effects occurring in the piezo-electric transducers; the Bragg-grating sensors in such case can be assumed to be deterministic in their sensing characteristics, and are optionally temperature-compensated in their sensing characteristics by including a temperature sensor in thermal contact with the waveguide 200. Optionally, the temperature sensor is implemented using Bragg-filter grating structures. Such feedback is beneficial because it enables the apparatus 180 to maintain its calibrated measuring accuracy better over a prolonged period of use in challenging environments.

As aforementioned, the waveguide 200 has a thickness radially from the conduit 100 which is substantially similar to a thickness of the wall of the conduit 100. Moreover, the waveguide 200 is beneficially fabricated from a mutually similar material to that employed for fabricating the wall of the conduit 100. Optionally, the waveguide 200 is integral with the wall of the conduit 100. Optionally, the waveguide 200 has a rectangular cross-section, with an aspect ratio in a range of 1:1 to 1:100, more optionally in a range of 1:1 to 1:20, and yet more optionally in a range 1:1 to 1:10. Optionally, the waveguide 200 is fabricated from a solid metal. Optionally, the waveguide 200 is fabricated, at least in part, from a composite material and/or a sintered material. Such a sintered material includes, for example, lead zirconite titanate (PZT) or similar ceramic material, such that the cluster of transducers 220 is formed integrally with the waveguide 200 by locally polarizing distal regions of the waveguide 200 during manufacture. Optionally, the waveguide 200 has a thickness in a range of 5 mm to 5 cm, and more optionally in a range of 8 mm to 3 cm.

By employing aforementioned features into the waveguide 200 and its associated cluster of transducers 220, edge, symmetric, anti-symmetric or shear horizontal families of modes can be selectively excited using piezo-electric elements for compressional, shear vertical or shear horizontal excitation, respectively. Optionally or additionally, excitation of top and bottom planes of the distal end of the waveguide 200 can be used to enhance symmetric or anti-symmetric modes. When top and bottom plane excitation is employed for the cluster of transducers 220, the selection between symmetric and anti-symmetric modes can be performed electronically, for example operating the elements in-phase or out-of-phase. Such a manner of implementation enables the waveguide 200 to have a broader bandwidth in comparison to known conventional ultrasonic transducers, namely rendering the waveguide 200 highly suitable for use in accurate temporal pulse measurement methods, for example time-of-flight (TOF) measurement methods.

Optionally, at least one distal end of the waveguide 200 includes one or more damping features or structures to absorb back-and-forth propagation of acoustic radiation along the waveguide, namely end-to-end reflections, thereby assisting to reduce a tendency for standing waves to be established within the waveguide 200 when in operation; this provides for acoustically cleaner operation of the waveguide 200, thereby potentially increasing measurement signal-to-noise ratio and mode selectivity. The one or more damping features are optionally implemented using damping materials applied onto transducer waveguide 200, and/or by a form of active feedback using transducers supplied with anti-phase signals. Such active feedback is optionally implemented in an adaptive iterative manner, to accommodate changes in characteristics of the waveguide 200 and/or the conduit 100 over a prolonged period of use, for example a 20 year period, to ensure that effective dampening is reliably achieved.

In respect of the waveguide 200, an acoustic wave transmitted thereto is directed along the line of propagation in the transducer waveguide. For Lamb modes, the transducer waveguide is optionally as narrow as a thickness of the waveguide, namely a 1:1 aspect ratio in cross section, but is optionally wider. When used with the conduit 100, the transducer waveguide 200 thickness boundaries are beneficially curved in accordance to the conduit 100 curvature, and directed.

The apparatus 180 of the disclosure described above provides numerous benefits in comparison to many types of known flow meters. In a known ultrasonic "clamp-on" type flow meter, namely single-phase meters, acoustic radiation is transmitted in a radial manner in a cross-section of a given pipe, and at an angle determined by a wedge-element geometry employed in the known flow meters. As a result, measurement occurs primarily at a central region of the given pipe, such that, when the given pipe is gas-filled at its centre and a remainder of the pipe is liquid-filled, transmission of acoustic radiation is severely affected, potentially resulting an no flow measurement being possible to obtain. Apparatus pursuant to the present disclosure are thus capable of providing major benefit in comparison to known single-phase flow meters.

The apparatus 180 is capable in operation, by selectively acoustic exciting sectors of the inner volume of the conduit 100 for measurement purposes, wherein the sectors define a "circle of construction" denoted by 270, wherein sensing occurs in an annular region which lies radially outwards from the "circle of construction" 270, and wherein the "circle of construction" 270 has a radius which is defined by selective steering Lamb-wave acoustic modes within the waveguides 200A, 200B following a helical path within the wall of the conduit 100 and/or by varying a frequency of the Lamb-wave acoustic modes excited by the elements 220 in the waveguides 200A, 200B following a helical path within the wall of the conduit 100. By taking a series of measurements for the sectors for a range of "circles of construction" 270, data is obtained from the acoustic radiation, when received as aforementioned, to compute a spatial tomographic representation of the flow 110 within the inner region of the conduit 100.

Referring to FIG. 4, a transverse cross-section illustration of the conduit 100 of FIG. 3 is shown, wherein three sets of waveguides 200(1), 200(2), 200(3), are disposed at 120° intervals around an external circumference of the conduit 100; each set includes two transducers, for example as illustrated in FIG. 3. The conduit 100 encloses a volume 260 in which the flow 110 occurs in operation. The three sets of waveguides 200(1), 200(2), 200(3) in temporal sequence are operable to emit beams, for example denoted by 250, of acoustic radiation, for example ultrasonic radiation but not limited thereto, into the volume 260 for use in characterizing the flow 110; such temporal sequence of beam emission enables angular sectors of the three sets of waveguides 200(1), 200(2), 200(3) to be selectively monitored, as aforementioned. The three sets of waveguides 200(1), 200(2), 200(3) are beneficially fabricated to follow spatially a substantially helical path along a length of the conduit 100. Beneficially, the three sets of waveguides 200(1), 200(2), 200(3) have a radial thickness which is substantially similar to a wall thickness of the conduit 100; moreover, the three sets of waveguides 200(1), 200(2), 200(3) are beneficially fabricated from a similar material to that of the wall of the conduit 100, or at least fabricated from a material which has substantially similar mechanical material density and Young's modulus characteristics to that of the material of the wall of the conduit 100. By "substantially similar" is meant to be within a range of 80% to 120%, more optionally a range of 95% to 105% similar density and Young's modulus properties. Optionally, the three sets of waveguides 200(1), 200(2), 200(3) are operable to support propagation of substantially a single helical acoustic radiation mode; alternatively, the three sets of waveguides 200(1), 200(2), 200(3), have a lateral width to their waveguide structures which enables several helical acoustic modes to be selectively propagated therein, for example by selecting an excitation frequency for the acoustic modes, and/or by employing the cluster of elements 220 as a phased array transmitter, wherein varying relative amplitudes and/or phases of drive signals applied to the cluster of elements enables acoustic mode steering within the three sets of waveguides 200(1), 200(2), 200(3) to be achieved, and corresponding steering of acoustic beams of radiation coupled to a region within the conduit 100.

The three sets of waveguides 200(1), 200(2), 200(3) are optionally integrally formed with the wall of the conduit 100, for example by at least one of: a machining process, a milling process, a grinding process, a brazing process and/or a spark-erosion process. Alternatively, the three sets of waveguides 200(1), 200(2), 200(3) are coupled via a coupling compound which is interposed between three sets of waveguides 200(1), 200(2), 200(3) and an external surface of the conduit 100. Yet alternatively, three sets of waveguides 200(1), 200(2), 200(3) are applied to the external surface of the conduit 100 in a clamp-on manner. The wall of the conduit 100 is beneficially fabricated from carbon steel, stainless steel, a composite material, or another metal such as aluminium, copper or similar. Such a composite material is, for example:

(i) a fibreglass composite pipe, for example suitable for conveying water supplies;

(ii) a silicon carbide composite pipe, for example suitable for use for guiding flow flows in nuclear facilities, and so forth.

Referring to FIG. 4, a combination of acoustic beams propagating through a central axis of the conduit 100, and also through regions of the volume 260 away from the central axis of the conduit 100, namely "off-axis", excited at a plurality of different angles, provide a measurement of spatial fluid flow velocity for an entire cross-section of the volume 260, wherein the measurement provides an indication of flow velocities as a function of spatial position within the volume 260. When the apparatus 180 is suitably designed, the measurement is capable of being within a fiscal measurement requirements, for example in laminar flow conditions devoid of turbulent flow. Each of the three sets of waveguides 200(1), 200(2), 200(3) is, for example, operable to generate in operation a plurality of off-axis chordal acoustic radiation propagation paths which enable a corresponding angular sector of an internal cross-section of the conduit 100 to be interrogated. The three sectors of the waveguides 200(1), 200(2), 200(3) defines a corresponding "circle of construction" 270, as aforementioned, wherein interrogation of an annular region between the "circle of construction" 270 and an inner surface of the conduit 100 to be characterized. By employing a series of measurements with varying radii of the "circles of construction" 270, as complete spatial tomographic analysis of the inner region of the conduit 100 is achievable in operation. Such tomographic analysis involves populating a matrix of data with measurement for different radii of circles of construction 270, and then solving multiple simultaneous equations represented by the matrix to derive component signals from an array of location across the cross-section of the volume 260. As aforementioned, such solution of multiple simultaneous equations is beneficially achieved using a array of processors, as in a digital array processor. The array of processors are beneficially RISC machines, as aforementioned, for example as manufactured by ARM Holdings, United Kingdom.

The apparatus 180 illustrated in FIG. 3 and FIG. 4, with its associated signal processing arrangement, is capable of measuring the flow 110 in both laminar flow conditions and turbulent flow conditions, for example by suitably reconfiguring itself, as will be described in more detail later. An onset of turbulence occurs in the flow 110 when its Reynolds number $R_e$ exceeds a threshold value, as will next be elucidated. The Reynolds number $R_e$ is susceptible to being computed from Equation 1 (Eq. 1):

$$R_e = \frac{\rho V D}{\mu} \qquad \text{Eq. 1}$$

wherein $R_e$=Reynolds number, wherein a value $R_e$<2300 corresponds to a laminar flow, a value 2300<$R_e$<4000 corresponds to a transitional flow, and a value $R_e$>4000 corresponds to a turbulent flow;
V=fluid velocity of the flow 110;
ρ=a density of a fluid present within the volume 260;
μ=a fluid velocity the fluid present in the volume 260; and
D=a diameter of the pipe 100.

By employing off-centre acoustic beams, for example ultrasonic beams, for interrogating the volume 260, information is obtained from the volume 260 which enables the aforesaid signal processing arrangement to perform uncertainty reduction computations, wherein:

(i) by employing interpolation of a detailed flow profile of the flow 110 for Reynolds number computation, an accurate flow profile calculation is possible, for example for determining whether the flow 110 is laminar or turbulent, also including a viscosity computation; and (ii) computations can be performed for static and dynamic uneven flow velocities, for example for performing compensations for swirl and similar types of fluid motion within the volume 260.

In an event that the conduit 100 is required to convey the flow 110 including a large concentration of small bubbles, which potentially causes severe acoustic radiation attention, the apparatus 180 beneficially switches to performing time-gated pulsed Doppler acoustic reflection measurements upon the flow, wherein movement of the bubbles causes a shift in the frequency of reflected acoustic radiation relative to a corresponding frequency of interrogating acoustic radiation. By measuring a frequency spread of time gated pulsed Doppler acoustic radiation, a degree of turbulence in the flow of the bubbles can be determined by computation.

Referring next to FIG. 5, an illustration of where measurements are performed within the volume 260 is shown. In addition to the sets of waveguides 200(1), 200(2), 200(3), there are mounted receiving transducers 300A, 300B, 300C which are also disposed at angles of 120° around the external surface of the conduit 100. The waveguides 200 and the transducers 300 are operable to enable the apparatus 180 to sample in respect of at least four spatial points for performing flow rate computations and therefrom determining whether the flow 110 is laminar, represented by a curve profile 310, or turbulent, represented by a curve profile 320. Thus, spatial measurements of flow at on-axis and multiple off-axis positions within the volume 260 enables more information to be obtained regarding whether or not the flow 110 is laminar, transitional or turbulent.

Thus, in FIG. 5, there is shown a process pipe, denoted by the conduit 100, with three sets of acoustic transducer positions; however, it will be appreciated that more than three sets of acoustic transducer positions can be employed, for example four or more sets. Dotted lines with arrow ends within the process pipe represent three transducer acoustic beam paths, wherein all the paths propagate through a central axis of the process pipe. Moreover, solid lines with arrow heads represent three transducer beam paths which are off-centre in respect of the aforesaid central axis. A laminar flow denoted by the curve 310 as depicted in FIG. 5 is generally approximately similar to the turbulent flow denoted by the 320, unless a spatial distribution of the flow 110 become temporally uneven, for example as a result of vortex generation. Flow velocities computed for the three off-axis positions provide sufficient information for the flow velocity profile to be determined in operation. FIG. 5 pertains both the liquid and gas flows within the conduit 100.

In comparison, a known type of flow meter will generally propagate acoustic beams in a direction orthogonal to a wall of the conduit 100; the apparatus 180 pursuant to the present disclosure employs non-orthogonal direction acoustic beams in addition of orthogonal acoustic beams, and thereby is able to extract more information from the flow 110 to determine its nature, for example whether it is laminar or turbulent. Any gas introduced into a liquid phase present in the conduit 100 will result in an attenuation of the aforesaid acoustic beams; such measurement pertains:

(i) in situations of a liquid flow within the conduit 100;
(ii) in situations wherein multiphase flows occur within the conduit 100; and
(iii) in situations wherein gas flow with liquid fraction occurs in the conduit 100.

Thus, both off-centre and on-centre acoustic beam interrogation of the volume 260 is required for performing flow rate measurement involving a gas fraction in liquid, mutatis mutandis a liquid fraction present in a gas.

The sensor apparatus 180 pursuant to this disclosure is beneficially operable to employ at least three different strategies for non-invasive acoustic beam interrogation of the volume 260 by employing off-centre acoustic beams, namely:

(a) an acoustic beam interrogation of the volume 260, wherein there is beneficially employed a beam 250 having divergent angle of greater than 10°;
(b) a steered phase-array interrogation of the volume 260; and
(c) a measurement of transducer geometry and mounting orientation onto the conduit 100.

Optionally, shear-mode acoustic radiation generation is employed when implementing one or more of (a) to (c) within the sensor apparatus 180.

When wide-beam excitation is employed via chordal path excitation when using the sensor apparatus 180, Lamb wave propagation is beneficially employed, wherein Lamb wave or wide beam sensors operate by emitting acoustic energy at various frequencies through the conduit 100 for locating a frequency which most closely matches a natural propagation frequency of acoustic radiation within a wall of the conduit 100. When the transducers 200, 300 are operated at such a matched frequency, acoustic radiation substantially at the matched frequency is transmitted into the flow 110 within the volume 260, with the wall of the conduit 100 functioning as a waveguide. As aforementioned, the wide beam of acoustic radiation travels outside the central axis of the conduit 100, and can be received at a convenient location using one or more of the transducers 300A, 300B, 300C. Optionally, as will be elucidated in greater detail later, the transducers 300A, 300B, 300C are beneficially implemented using Bragg-filter-grating transducers. Optionally, the Bragg-filter-grating transducers employ anti-phased-filter-gratings, so as to define for each anti-phase-filter-grating a null in its optical reflection characteristics which very accurately defines its grating periodicity, thereby increasing an operating signal-to-noise performance of the apparatus 180. Employing the Bragg-filter-grating transducers is especially beneficial, because there occurs in operation negligible crosstalk of electrical drive signals to the elements 200 to the Bragg-filter-grating transducers, as the former operates in an electrical regime and the latter operates in an optical regime; this lack of crosstalk is relevant when data processing parts of the apparatus 180 are deployed remotely from the transducers 300A, 300B, 300C, for example when the former is deployed at sea level, and the latter is deployed many kilometres away on an ocean floor.

The Bragg-filter-gratings are optionally interrogated using optical wideband light sources, for example light emitting diode (LED) sources, or from optical swept-frequency sources. Moreover, the Bragg-filter-gratings are optionally formed into a single length of optical fibre, thereby reducing a number of signal connections to be made between the data processing parts of the apparatus 180 and the transducers 300A, 300B, 300C, Referring to FIG. 6, the transducers 200A, 200B are optionally operable to emit acoustic radiation beams 250(A), 250(B) in forward and backward directions respectively relative to the flow 110, so that a differential measurement of the flow 110 can be performed, using the transducer 300 as a receiving transducer. The transducer 300 is within the wide-angle emitted beams 250(A), 250(B) as illustrated. Beneficially, phased-array transducers are employed for implementing the transducers 200A, 200B so that they are able to be used to measure flow velocities at various off-axis positions, for example as illustrated in FIG. 5.

Acoustic radiation beam emissions from the transducers 200 illustrated in FIG. 7 are beneficially steered within the volume 260 by implementing the transducers 200 as phased arrays of acoustic emitting elements, for example driven by a plurality of signals S1 to S4 which are temporally shifted relative to one another to define a given angle of the beam 250 relative to the conduit 100 and its internal volume 260. Optionally, one or more elements of the phased arrays of elements forming the transducers 200 are assembled directly onto the external surface of the conduit 100, as illustrated in FIG. 8, or are assembled together into a transducer unit which is attached to the external surface of the conduit 100, for example as illustrated in FIG. 7.

Referring next to FIG. 9, an embodiment of the apparatus 180 is shown, wherein phased-arrays of elements are coupled to waveguides 200A, 200B, 200C to couple acoustic radiation into the volume 260 of the conduit 100 for steering acoustic radiation beams within the volume 260 in operation, for example for providing one or more on-axis beams traversing the central axis of the conduit 100, as well as one or more off-axis beams. Receiver transducers 300 are beneficially implemented in an array format, for example using a network of Bragg-grating-sensors based upon use of optical fibre components, as will be described in greater detail later. The waveguides 200A are optionally mounted in a spiral manner, namely a spatially helical manner, around the external surface of the conduit 100, as illustrated. Alternatively, the waveguides 200A are implemented as a broad collar which is bonded or clamped to the external surface of the conduit 100. Thus, the present disclosure includes adding guided-wave sensors in a grid configuration around the conduit 100 for picking up guided-wave signals from, for example, three sets of guided-wave transducers 200 in a 0°, 120° and 240° formation around the pipe 100, as illustrated. The 0°, 120° and 240° formation, corresponding to aforementioned sectors, define radial "circles of construction" for measurement for the apparatus 180, for example when performing spatial tomographic profiling of the volume 260. Optionally, other angles of deployment are employed, for example 0°, 90°, 180°, 170°, or even 0°, 60°, 120°, 180°, 240°, 300°.

Referring next to FIG. 10, there is shown an illustration of an alternative embodiment of the apparatus 180, wherein three sets of guided wave transducers 200 are disposed at 120° angular positions around the conduit 100; guided wave transducers 200 are shown mounted in a linear format, they are alternatively beneficially mounted in a helical format, as described in the foregoing. Moreover surface mounted receiver transducers 300 are mounted at intervals around a circumference of the conduit 100 at a plurality of locations along a length of the conduit 100. The guide wave transducers 200 are intermingled with the receiver transducers 300, as illustrated. The receiver transducers 300 are beneficially implemented as a grid network of Bragg-grating filter transducers, for example mounted against the external surface of the conduit 100, or partially embedded into the external surface, for example in conformal reference indentations. Optionally, each transducer 300 is bonded or clamped to the external surface of the conduit 100 at a point mount adjacent to its Bragg grating, and a coupling fluid or gel is used to couple the Bragg grating to the external surface. Such a manner of mounting reduces thermal stresses on the Bragg grating, and thus potentially improved operating reliability of the apparatus 180 in challenging situations of use.

The receiver transducers 300, namely surface detectors, are beneficially located in three bands 400, 410, 420, substantially extending around a circumferential region of the conduit 100. First and third bands 400, 420 of the surface detectors are located in areas from which guided acoustic waves from the transducers 200 of the transducers sets 200(1), 200(2), 200(3) hit the wall of the conduit 100 after reflection. A second band 410 of the surface detectors is located in an area in which the acoustic guided waves hit an opposite wall of the conduit 100.

Referring next to FIG. 11, there is shown an illustration of the receiver transducers 300 for sensing an arrival of a wide acoustic beam emitted from the guided wave transducers 200; by "wide", is meant greater than 5° beam divergence angle, more optionally greater than 10° divergence angle. On account of the receiver transducers 300 being disposed in a circumferential manner around the external surface of the conduit 100 as shown, acoustic beams emitted from the three sets of transducers 200(1), 200(2), 200(3) are susceptible to being detected by the receiver transducers 300. Optionally, the receiver transducers 300 are implemented, as aforementioned, as a surface detector grid consisting of a plurality of acoustic detectors 450 having physical contact with the external surface of the wall of the conduit 100. Beneficially, the acoustic detectors 450 are connected to a signal processing arrangement, for example to a control unit wherein each detector 450 has an individual signal channel associated therewith. The acoustic detectors 450 are optionally implemented using aforesaid Bragg-grating filter sensors (Fibre Bragg Gratings, "FBG"), but are susceptible to being implemented in alternative manners, for example utilizing one or more of:

(i) piezo-electric transducers;
(ii) accelerometers;
(iii) microfabricated electronic mechanical devices (MEMs), for example micromachined microfabricated Silicon accelerometers and/or microphones;
(iv) any other type of substantially point sensor which is operable to detect acoustic radiation;
(v) any other type of spatially discriminating fibre optic sensing method which is operable to detect acoustic radiation.

Bragg-grating filter sensors are especially beneficial in that multiple acoustic sensing points can be established along a length of a single optical fibre which is attached to the external surface of the conduit 100 to form a grid or band of sensors; optionally, the single optical fibre is looped in one or more pigtails between the Bragg-grating filter sensors. Optionally, the Bragg-grating filter sensors are formed using photolithographic etching processes, or by stress impression processes by impressing a grating mandrel against the optical fibre; such processes are described in greater detail later. Optionally, the Bragg-grating filter sensors are fabricated from fused silica material. When the apparatus 180 is to be used in environments where high doses of ionization radiation are likely to be encountered, for example in nuclear waste reprocessing plants, in nuclear reactors, for example Thorium LFTR apparatus wherein high neutron fluxes and high Gamma radiation fluxes are likely to be encountered, the Bragg-grating filter sensors are beneficially optionally fabricated from sapphire monomode optical fibres. Thorium LFTR apparatus is, for example, potentially useable for transmuting MOX nuclear waste to render it environmentally relative benign by transmutation processes. Optical fibres are susceptible to high temporal rates of sensing, are insensitive to local electrical interference in operation, and are potentially very compact. Such compactness enables the acoustic detectors to be implemented using a plurality of optical fibres, thereby providing inbuilt redundancy in an event that one of the optical fibres were to fail when in service, for example in a sea-bed location, potentially several kilometres deep with ambient pressures in an order of 150 Bar or more.

Referring next to FIG. 12, there is shown a schematic illustration of a Bragg filter grating sensor indicated generally by 500; this sensor is also referred as being a "fibre Bragg grating sensor" (FBG). An optical fibre 510 includes an optical cladding 520 and an optical core 530. In operation, optical radiation propagates along the optical core 530 to which it is substantially confined by internal reflection occurring on account of the cladding 520 and the optical core 530 having refractive indexes $n_2$, $n_1$ respectively, wherein $n_2$ and $n_1$ are mutually different. The optical fibre 510 is optionally a multi-mode optical fibre, alternatively a mono-mode optical fibre. An optical grating 540 can be formed in the optical core by removing a portion of the cladding 520 in a region of the grating 540 to expose the optical core 530, by processing the optical core 530, for example by photolithographic steps followed by chemical or ion-beam milling, to modify its refractive index to form the grating 540, and then the removed cladding 520 restored by adding a polymer or glass material having a refractive index of substantially $n_2$. The grating 540 has a spatially varying refractive index having a period of λ, wherein optical radiation propagating in the optical core 530 have a wavelength therein similar to the period λ experiences a point optical impedance mismatch, resulting in a portion of the optical radiation being reflected back along the optical fibre 510 as illustrated, and a correspondingly reduced amount of optical radiation being transmitted further along the optical fibre 510. As the grating 540 is stretched and compressed by acoustic radiation acting thereupon, the wavelength at which partial reflection of optical radiation occurs at the grating 540 is modified. Such a shift in wavelength, which is modulated by the received acoustic radiation at the grating 540, is detected in the aforesaid signal processing arrangement to generate a signal representative of the acoustic radiation received at the grating 540.

Referring next to FIG. 13, there is shown an illustration of the optical fibre 510 disposed upon the external surface of the conduit 100, disposed in a spatial region between the transducers 200A and 200B, wherein the transducers 200A, 200B corresponding to a set of transducers 200(1). The optical fibre 510 has a plurality of gratings 540 therealong. By meandering the optical fibre 510, a grid of detection points is established on the conduit 100 for detecting acoustic radiation thereat in operation. Beneficially, the optical fibre 510 is folded in a radius of curvature at ends of meanders which is greater than substantially fifteen times a diameter d of the optical fibre 510. Thus, one optical fibre is capable of addressing many individually-addressable acoustic radiation sensor points. Moreover, the optical fibre 510 can be coupled to the signal processing arrangement which is remote, for example a distance of 1 km or more remote from the gratings 540. A free-end of the optical fibre 510 which is remote from the signal processing arrangement is beneficially terminated in a substantially non-reflecting optical load, to prevent spurious reflections back-and-forth between ends of the optical fibre 510.

Referring next to FIG. 14, the signal processing arrangement if represented by a light source and sensor 600, for example a solid-state laser or a high-brightness light emitting diode (LED), coupled to a photodiode detector, alternatively a Mach-Zender-interferometer-based optical detector. Beneficially, the source and sensor 600 is coupled to a signal controller 610 for handling signals being input to and output from the source and sensor 600. As illustrated, the data processing arrangement, via an optical junction 620, is able to service several optical fibre 510 detector arrays attached to the external surface of the conduit 100. The optical fibre 510 is beneficially employed in petrochemical environments to reduce a risk of explosion hazard which may pertain to transducers which require directly-applied electrical signals for their operation. A 6×4 grid of gratings 540 is shown. The source and sensor 600, in combination with the signal controller 610 constitute a signal processing arrangement. The signal processing arrangement is beneficially, at least in part, implemented using computing hardware, for example one or more high-speed low-power-consumption RISC processors, for example manufactured by Arm Holdings (Cambridge, United Kingdom), which are able to process acoustic radiation signals in real-time, for example performing time-of-flight computations, correlations, convolutions and such like. The computing hardware is beneficially operable to execute one or more software products recorded on non-transient machine-readable data storage media, for example solid-state data memory, for implementing one or more algorithms for enabling the apparatus 180 to function as described.

Thus, a sensor mounted sensor network as illustrated in FIG. 14 covers a significant number of positions around a cross-section of the conduit 100 in combination with three or more wide-beam transducers 200, thereby sensing at many points within the region or volume 260. Information obtained from each traverse enables the data processing arrangement to detect one or more of:
(i) a fluid velocity of the flow 110;
(ii) a speed of acoustic radiation propagation within the region or volume 260.
(iii) a diameter of the conduit 100 for detecting corrosion on an inside surface of the conduit 100;
(iv) an actual inner diameter profile of an actual position of measurement pipe for clamp-on flow meter applications, as pipe dimensional tolerances, for example ASME 831.3 standard for process piping, can vary greatly and to the extent the unknown dimension represents the most significant measurement uncertainty contribution to the flow measurement system.

Situations potentially arise for the apparatus 180 that solid build-up in the conduit 100 occurs, resulting in a considerable change in effective pipe cross-section area, for example as illustrated in FIG. 2, situation C; however, the apparatus 180 is capable of correcting for such cross-sectional area by monitoring a dynamic effective cross-section of the conduit 100 by way of its multiple approaches to interrogating the region or volume 260.

The apparatus 180 is capable of enabling a quantitative analysis of received acoustic signal attenuation when a gas fraction is present within the conduit 100, for example caused by a gas volume 700 present in the conduit 100, as illustrated in FIG. 15.

Referring next to FIG. 16, there is shown an illustration of three pairs of Lamb-wave transducer configurations, for example using three sets of aforesaid transducers 200. Each pair of transducers 200 is operable to excite, via Lamb waves induced in the wall of the conduit 100 following helical paths therein, acoustic beams 250 in up-flow and down-flow directions, for example for making a differential measurement. When the flow 110 is homogeneous in which a gas volume, moves with a liquid flow, the apparatus 180 is operable to perform following actions:
(i) to identify whether the fluid is predominantly water or oil, or a mixture of two liquid fractions;
(ii) to measure a flow velocity of the fluid flow 110;
(iii) to perform a liquid flow rate measurement through liquid velocity measurement, less gas volume/velocity influences;
(iv) to identify any non-homogeneity as a gas volume A restricted gas volume in liquid present in the region or volume 260 of the conduit 100 will attenuate and/or scatter Lamb wave energy which is coupled from the transducer 200 through the wall of the conduit 100 into the region or volume 260; for example, in certain operating situations, the amount of gas present within the volume 260 is so great, that the apparatus 180 is operable to switch to employing Doppler measurement, for example time-gated Doppler measurement, of acoustic radiation reflected from the bubbles in order to computer a velocity of the flow 110. Beneficially, a pure liquid flow velocity is computed for a given situation by a computation of acoustic radiation transit time between transmitting and receiving transducers, namely between transducers 200A, 200B or 200, 300 as appropriate. A size of the bubble 700 is determined by a size of acoustic "shadow" generated behind the bubble 700, as illustrated in FIG. 15; such shadow is beneficially detected spatially using the transducer 300, namely grid array of gratings 540 disposed around the external surface of the conduit 100.

The transducer 300, for example implemented as the grid array of Bragg-grating sensors 540, enables spatial monitoring of the cross-section of the conduit 100 to be achieved, for example to detect regions of oil, water and gas. Such cross-section monitoring, namely "tomographic monitoring", is achieved using multiple acoustic beams 250 from the three or more sets of transducers 200. Beneficially, following measurements are made using the apparatus 180 when in operation:
(i) a volume 810 between the transducer 200A and an area of reflection 820 at an opposite inside wall of the conduit 100; and
(ii) a volume 830 between the area of reflection 820 and an area whereat reflected acoustic radiation is received, for example at the transducer 200B.

Beneficially, such measurement is made for at least all three sets of transducers 200(1), 200(2), 200(3), thereby mapping six different regions of the region or volume 260, by way of the acoustic radiation being reflected at the inside wall of the pipe 100, as illustrated. By such an approach, annular measurements are made of the flow 110, in an off-axis manner, from an inner wall of the conduit 100 to a "circle of construction" defined by an inner extent of the flow 110 which is interrogated by the beams 250. The "circle of construction" has a diameter which is varied by controlling an angle of an acoustic mode excited by the transducers 200, and/or a frequency of the excited mode. Tomographic (tomometric) processing of signals received at the transducers 200(1), 200(2), 200(3), enables a spatial tomographic measurement of the flow 110, and phases present in the flow, to be computed.

Operation of the sensor apparatus 180 to measure a complex flow within the conduit 100 will now be described in greater detail:
(a) Liquid fraction measurement, for example oil and water: the acoustic radiation velocity for each wide angle acoustic radiation beam 250 is calculated for a large number of beams 250, for example using time-of-flight measuring techniques, to an extent that this represents an acoustic radiation velocity profile for an actual fluid volume present in the conduit 100 for a specific duration of time. The acoustic radiation velocity profile represents a profile for a presence of oil and water, and hence a volumetric fraction of water and oil can be calculated therefrom in the sensor apparatus 180;
(b) Gas fraction measurement: information derived from multiple excited acoustic radiation beams is employed for performing such measurements, wherein significant attenuation or complete attenuation is indicative of a presence of gas. Beneficially, in the sensor apparatus 180, such information is obtained from a large number of acoustic radiation beams 250, providing representative information of gas being present within the region or volume 260;
(c) Liquid fraction velocity measurement: such measurements are beneficially performed by employing time-of-flight of one or more beams 250 of acoustic radiation to propagate within the volume or region 260, with the sets of transducers 200 being excited in forward and reverse direction relative to a direction flow 110 within the conduit 100; alternatively, or additionally, cross-correlation measurements based of liquid-fraction acoustic radiation propagation velocity as a signature is employed for monitoring movement of the liquid fraction for determining its corresponding velocity or movement; and (d) Gas fraction velocity: this is computed as described in the foregoing.

Optionally, the complex flow is defined a continuous liquid based upon given percentages of acoustic radiation signals received at the transducers 300, for a signal attenuation less than a defined threshold, expressing no influence of gas upon the measurement. Optionally, sequential shift between two or more acoustic radiation frequencies is beneficially employed to enhance contrast in signal attenuation experienced between liquid and gas phases present in the conduit 100.

Next, measurement of a continuous gas complex flow within the conduit 100 will be described. When implementing such measurement:

(e) Gas fraction measurement: the acoustic radiation propagation velocity within the region or volume 260 of the conduit 100 is computed for a large number of acoustic radiation beams 250, to an extent that this represents an acoustic radiation velocity profile for an actual fluid volume during a specific duration of time. Such acoustic radiation propagation represents a profile for the presence of oil and water, thereby enabling a volumetric fraction of water and oil within the region or volume 260 of the conduit 100 to be computed;

(f) Liquid fraction measurement, for example a flow of mist: information pertaining to multiple acoustic radiation beams 250 propagating within the region or volume 260 of the conduit 100, at one or more points of expected arrival is utilized; any significant attenuation, or complete attenuation, is indicative of a presence of a liquid. Beneficially, such information is obtained from a large number of acoustic radiation beams 250, wherein representative information is employed to determine gas presence in the region or volume 260 of the conduit 100; and (g) Gas fraction velocity: gas fraction velocity if computed from time-of-flight measurements using acoustic radiation beams 250 propagating with and against the flow 110 of gas within the region or volume 260 of the conduit 100.

Optionally, different frequencies for the acoustic radiation employed in the beams 250 can be employed in such measurements to increase contrast, and hence measurement accuracy.

Next, measurement of transitional flows within the region of volume 260 of the conduit 100 will be described. When implementing such measurement:

(h) liquid and gas fractions are measured via measurement of acoustic radiation propagation velocities, for example by performing one or more time-of-flight measurements using the apparatus 180; and (i) fluid velocity measurements are performed by employing cross-correlation based on profile of acoustic radiation propagation pertaining to movement in the region or volume 260 is the conduit 100, for a defined time or by Doppler measurement, for example by employing a time-gated Doppler measurement.

In the data processing arrangement of the apparatus 180, for example as shown in FIG. 14, a flow computer computes information for aforementioned measurement strategies (a) to (i) in a parallel manner, namely:

(i) a single-phase liquid flow measurement computation;
(ii) a single-phase liquid flow measurement computation, namely including computation of gas impurities;
(iii) a dual-phase liquid flow measurement computation;
(iv) a liquid-continuous multiphase flow measurement computation;
(v) a transitional flow computation;
(vi) a gas-continuous multiphase flow measurement computation;
(vii) a single-phase gas flow measurement computation, taking into account a potential presence of one or more liquids; and
(viii) a pure gas flow measurement computation.

For each of the computations pertaining to (a) to (i), a dynamic measurement uncertainty is beneficially computed in the signal processing arrangement of the sensor apparatus 180, in real-time, in addition to computations for determining flow fractions and flow rate information. Beneficially, such uncertainty data is compared in real-time for a selection of computed measurement results to provide an aggregate form of sensor apparatus 180 output indicative of, for example, liquid fraction and flow rate.

In the foregoing, various strategies for the sensor apparatus 180 to compute output indicate of flow rate and fractions present are described. In the following description, features of the sensor apparatus 180 will be described in greater detail. Referring to FIG. 17, the optical fibre 510 and its associated Bragg grating sensors 540 are employed to provide a surface-mounted sensor network which is capable of providing secondary outputs from the signal processing arrangement of the sensor apparatus 180, for example:

(a) a surface temperature profile of the conduit 100, for example for detecting a process malfunction or build-up of solid onto the inside surface of the conduit 100; and
(b) detecting changes in guided wave signal propagation directly though the wall of the pipe, namely not via the region or volume 260, for detecting any changes in an integrity of the conduit 100, for example a material loss therefrom arising from erosion and/or corrosion, as well as fatigue damage, such as cracking of the wall of the conduit 100.

In FIG. 17, there is shown an illustration of a portion of the wall of the conduit 100 to which the optical fibre and its associated Bragg grating sensors 540 have been applied. Optionally, the optical fibre 510 is supported in a compliant backing material 860, for example fabricated from one or more polymeric materials, for example from a plastics material, which itself is supported onto a frame 870 to which a force F can be applied to ensure that the optical fibre 510 contacts onto the external surface of the pipe 100 in a stable and acoustically efficient manner. The backing material 860 is beneficially acoustically dissipative, likewise the frame 870, so that spurious acoustic radiation signals are not generated in the apparatus 180 when in operation. In the apparatus 180, use of the ultrasonic transducers 200 potentially enhances flow rate measuring accuracy for non-invasive acoustic radiation flow meters; such transducers 200 are beneficially also clamped or otherwise forced against the external surface of the conduit 100.

The aforesaid apparatus 180 is capable of functioning as a pipe surface-mounted acoustic sensor grid for extending functionality of flow meters by measuring spatial flow information. As aforementioned, the sensor apparatus 180 includes one or more, for example three, sets of transducers 200(1), 200(2), 200(3) mounted to the external surface of the conduit 100. The sets of transducers 200(1), 200(2), 200(3) are operable, when supplied with suitable drive signals, to generate Lamb waves within the wall of the conduit 100, wherein the Lamb waves propagate along helical paths within the wall of the conduit 100, and wherein the Lamb waves are coupled into the region or volume 260 of the conduit 100 wherein fluid flows in operation, wherein the Lamb waves propagate as corresponding steered acoustic radiation in a form of one or more beams 250 which spread slightly as they propagate towards an opposite wall of the conduit 100. At an area of the opposite wall of the conduit 100 whereat the one or more beams 250 are received, there are included one or more receiver transducers 300, for example implemented as an acoustic sensor grid implemented using Bragg grating sensors 540 formed in an optical fibre 510 as aforementioned, which are operable of sensing an arrival of a representative number of beams 250 of acoustic radiation propagating though the volume 260. The one or more receiving sensors 300 detect differences in properties of the one or more beams 250 of the acoustic radiation which arrive, for example in respect of their received amplitude and their time-of-flight, for an entire area in which the acoustic radiation propagates.

The acoustic radiation is reflected from the opposite wall and propagates through a further spatial volume within the volume of region 260, eventually arriving at a same side of the pipe from which the one or more beams 250 were originally emitted. On the same side, the one or more beams of acoustic radiation are received by one or more receiver transducers 300 and/or one of the transducers 200 of the sets 200(1), 200(2), 200(3) being employed. Optionally, by measuring the amplitude of a portion of the acoustic radiation emitted out to the opposite wall of the conduit 100 that is received back on the same side of the wall of the conduit 100, a fluid phase at a position of the transducers 200, 300 can be determined, as more energy is reflected in a presence of gas at the inner surface of the wall of the conduit 100.

Such a measurement procedure is repeated in an opposite direction, relative to a direction of the flow 110 through the conduit 100. Moreover, such backward and forward measurements are executed for each of the sets of transducers 200(1), 200(2), 200(3), for example repetitive in a cycle of measurement which are continuously repeated to provide real-time monitoring of the flow 110 within the conduit 100. Thus:

(a) sensed multiple-point information obtained regarding time-of-flight in a first direction of propagation is subtracted from corresponding multiple-point information for a second direction, wherein the first and second directions are mutually opposite; from such measurement a fluid velocity profile is determined;

(b) from measured time-of-flight and known corresponding time-of-flight information, for example expressed in a form of look-up table in the signal processing arrangement, acoustic radiation propagation distribution is computed for the volume or region 260 in which the acoustic radiation propagates, thereby enabling a spatial distribution of fluid phases within the conduit 100 to be determined; and (c) the multiple point detection of the one or more steered acoustic radiation beams 250 provides information regarding acoustic radiation propagation attenuation within the volume or region 260. A partial or complete attenuation of the propagating acoustic radiation is indicative of a local presence of process fluids having mutually significantly different densities, for example one or more gas bubbles in liquid, or one or more liquid droplets in a gas, depending upon a dominant fluid phase flowing long the pipe 100 incepted by the one or more steered acoustic radiation beams 250. The number of sensors 300 which experience acoustic radiation attenuation is indicative of projected bubble or droplet size, for example the bubble 700 in FIG. 15.

When the apparatus 180 is employed to measure complex transitional flows, namely pertaining to a transition between liquid and gas continuous flows, the signal processing arrangement is beneficially operable to employ a cross-correlation measurement based in acoustic radiation information signature associated with interrogating from the fluid volume 830 to the second fluid volume 820, or movement within the volume, measured by corresponding sensors 300, for example Bragg grating sensors 540, optionally replaces the fluid fraction and flow rate measurements.

Optionally, the distributed receiver transducers 300, for example implemented as Bragg grating filter sensors 540, detect changes in properties relating to fluids flowing through the conduit 100, for example solid transport in aforesaid fluids, wherein the solid is a wax, a hydrate, scale, in addition to a surface temperature of the conduit 100. Such information to be derived from primary steered acoustic radiation beams, and/or from secondary acoustic radiation, for example shear mode excitation and acoustic radiation by additional transducers added to the sensor apparatus 180.

Optionally, the receiver transducers 300, for example Bragg grating filter sensors 540, are employed to detect dimension of the conduit 100, for determining pipe degradation such as wall thinning, corrosion, erosion, cracking, pitting pipe coating thickness and other pipe integrity issues. Such information is beneficially derived primary steered acoustic radiation beams which are excited in the sensor apparatus 180, in addition to secondary acoustic radiation, for example shear mode excitation and acoustic radiation by additional transducers added to the sensor apparatus 180. Optionally, Rayleigh wave radiation, which is excited by side-mounted elements 220 of the waveguide transducers 200, is coupled into the wall of the conduit 100 for detecting structural characteristics of the wall, for example:

(i) scale build-up on the inside surface of the wall of the conduit 100;

(ii) embrittlement of the wall of the conduit 100, for example resulting from neutron flux embrittlement, mechanical stress embrittlement or similar;

(iii) micro-cracking of the wall of the conduit, for example arising from local impurities in material, for example metal, of the wall of the conduit 100, wherein corrosion around the impurities has progressively occurred with time.

Optionally, the sensor apparatus 180 is implemented by using one central controller, for example a data processing arrangement including computing hardware, for synchronizing all three or more transducers 200 and their associated surround receiver sensors 300. Spatial information, obtained via use of these transducers 200, 300 for interrogating the region or volume 260 of the conduit 100 through use of synchronous and repetitive excitation, enables laminar, transitional and turbulent multiphase flows within the conduit 100 to be analyzed. As described in the foregoing, at least six regions of the volume or region 260 are interrogated by the steered beams 250, when three transducers 200 are employed; optionally, these six regions are at least partially spatially overlapping. Fluid phase fraction % and a flow rate across a full cross-section of the volume or region 260 can be determined using the apparatus 180. When gas bubbles present within the conduit 100 causes attenuation of acoustic radiation propagating therein, the receiver transducers 300, for example implemented as a spatially-distributed grid of sensors 540, off-centre propagation of acoustic radiation is measured and shadowing caused by the gas bubbles is detected. Optionally, the transducers 200, for example implemented using aforesaid waveguide transducers, is beneficially excited at two or more frequencies in a sequential manner, for reducing uncertainty in measured signals, and thereby increasing measurement accuracy of the sensor apparatus 180.

Next, the sets of transducers 200, for example implemented in a helical manner will now be elucidated in greater detail. Referring to FIG. 3, the sets of transducers 200 are operable to direct and shape selected acoustic propagation modes for the aforesaid acoustic radiation, thereby ensuring improved utilization of emitted acoustic radiation within the conduit 100. The acoustic radiation 240, propagating for example as beams 250, is directed towards a similarly shaped receiving transducer 200; for example, the transducer 200A emits the acoustic radiation, and the transducer 200B receives the acoustic radiation after it has been reflected from an opposite wall of the conduit 100 relative to that on which the transducers 200A, 200B are mounted, as illustrated. Such a waveguide structure for the transducers 200A, 200B enables radiation corresponding to spurious unwanted acoustic radiation propagation modes to be rejected and thus not contribute to received acoustic radiation signals, as represented by output signals from the transducer 200B, in this example, thus increasing measurement signal-to-noise ratio and hence enhancing measurement accuracy.

In the transducers 200A, 200B, the waveguide therein is substantially untapered, namely is different to a conventional wedge-shape coupling element used to couple ultrasonic transducers to an external surface of a conduit or pipe. Beneficially, the transducers 200A, 200B employ a waveguide thickness which is substantially similar to that of the wall of the conduit 100, and a waveguide material which is substantially similar to that of the wall of the conduit 100. The waveguide of the transducers 200A, 200B is capable of reducing signal drifts in signals obtained in the sensor apparatus 180 that would otherwise arise if wedge-shaped coupling elements were employed. Moreover, the waveguide of the transducers 200A, 200B is capable of coupling acoustic radiation more efficient to and from the wall of the conduit 100. Furthermore, the elongate length of the waveguide of the transducers 200A, 200B, in conjunction with associated monitoring sensors 230 enables an acoustic velocity within the transducers 200A, 200B to be determined, thereby enabling a temperature compensation of transducer 200 characteristics to be performed by the data processing arrangement of the sensor apparatus 180. Additionally, the monitoring sensors 230 enable operating integrity of the transducers 200A, 200B to be verified, for example equipment failure detection, which may be potentially relevant when the sensor apparatus 180 is a critical part of a petrochemicals facility, materials processing facility, power station, nuclear facility and similar.

Figure 18:
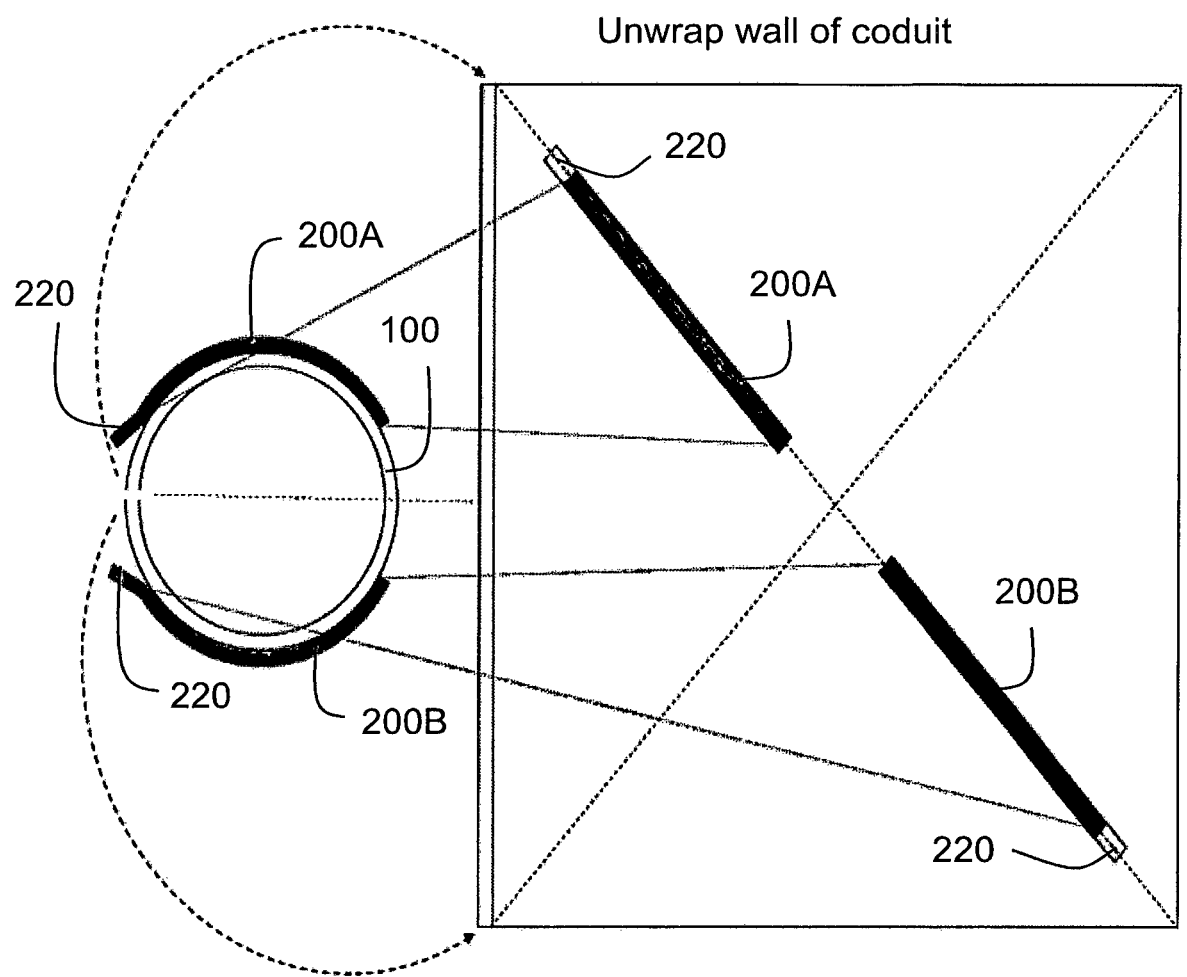
Figure 19:
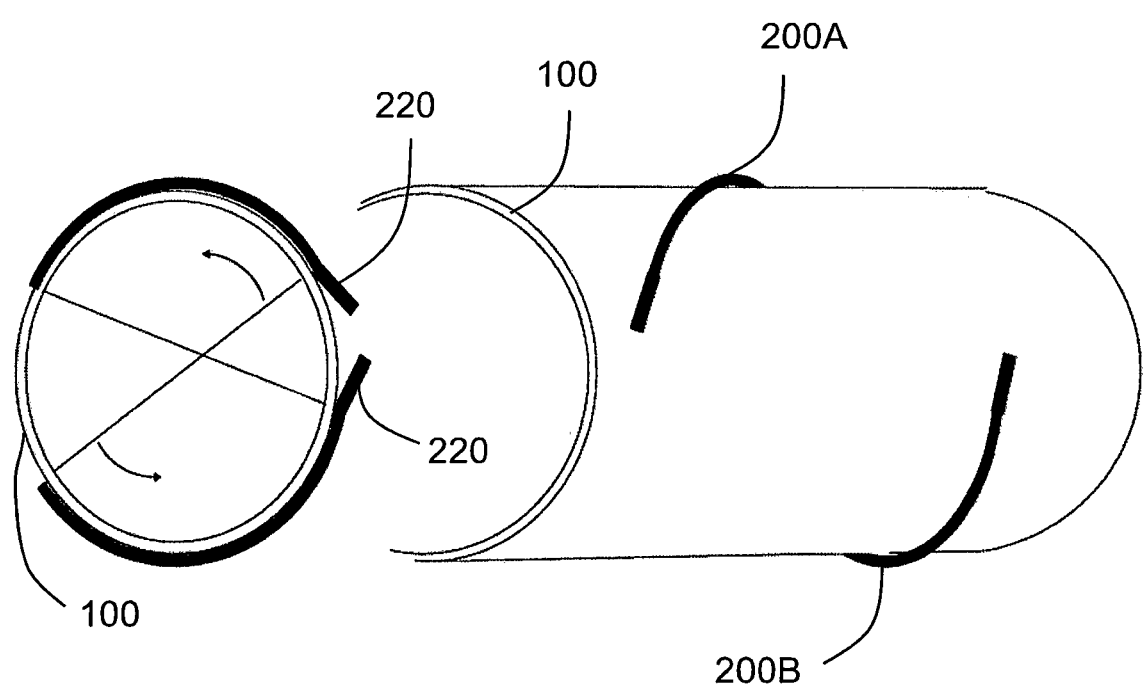
Figure 20:
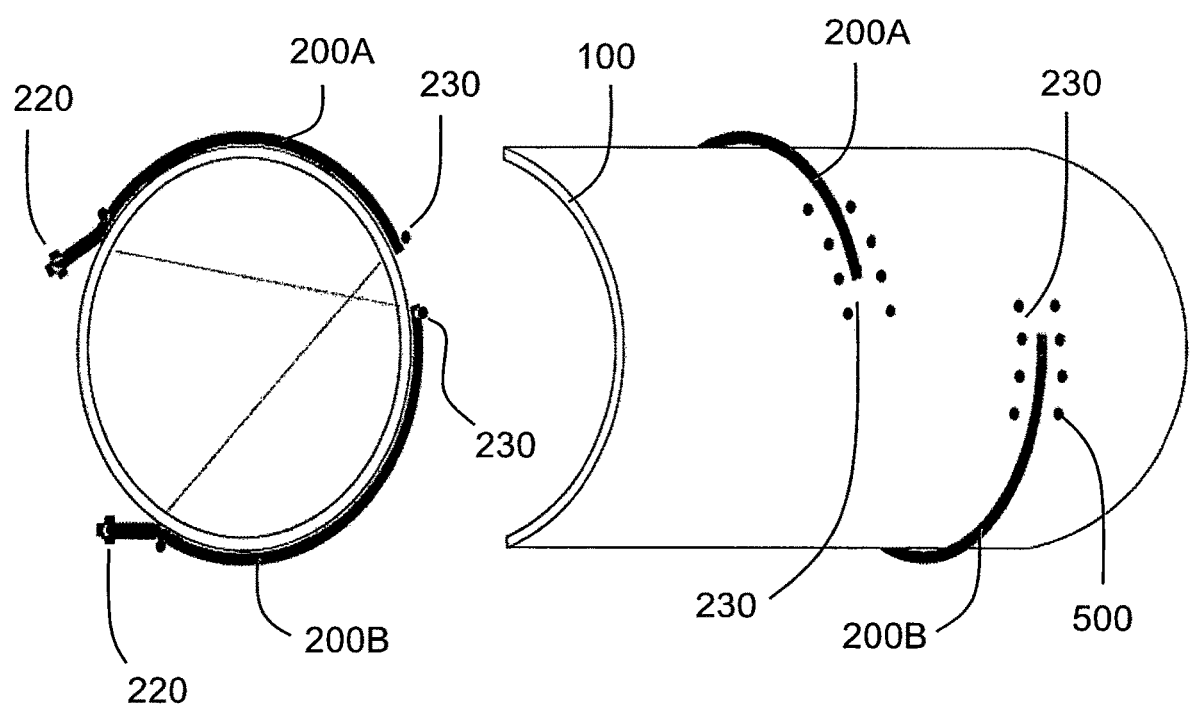

Referring next to FIG. 18, a helical manner of implementing the waveguide 200 is illustrated in further detail. Theoretically, if the conduit 100 were to be sliced on one side along its length and unwrapped, as shown, the waveguides 200A, 200B would be elongate liner structures. The waveguides 200A, 200B are beneficially mounted so that their elongate axes mutually align, as illustrated. In operation, Lamb-wave acoustic radiation is capable of propagating along the wall of the conduit 100 from the waveguide 200A to the waveguide 200B, and vice versa. By varying a frequency of operation, acoustic radiation is forced to following multiple chordal paths, defining a sector in which sensing occurs, within the volume 260 when propagating from the waveguide 200A to the waveguide 200B, and vice versa. When the wall of the conduit 100 is theoretically wrapped to form the conduit 100 as illustrated in FIG. 19, the waveguide 200A, 200B assume a helical format, as illustrated. As illustrated in FIG. 20, Brag-filter-grating (FBG) sensors, denoted by 230, are beneficially disposed at ends of the waveguide 200A, 200B, namely at an end remote from the cluster of elements 220 used to excite acoustic radiation within the waveguides 200A, 200B. Optionally, as illustrated, the waveguides 200A, 200B have an angle of expanse of circa 120°, for example in a range of 60° to 180°, and are disposed on substantially mutually opposite sides of exterior sides of the external surface of the wall of the conduit 100, as illustrated. In contradistinction, known wedge-shaped transducers typically have an angle of expanse of less than 10°.

Figure 21:
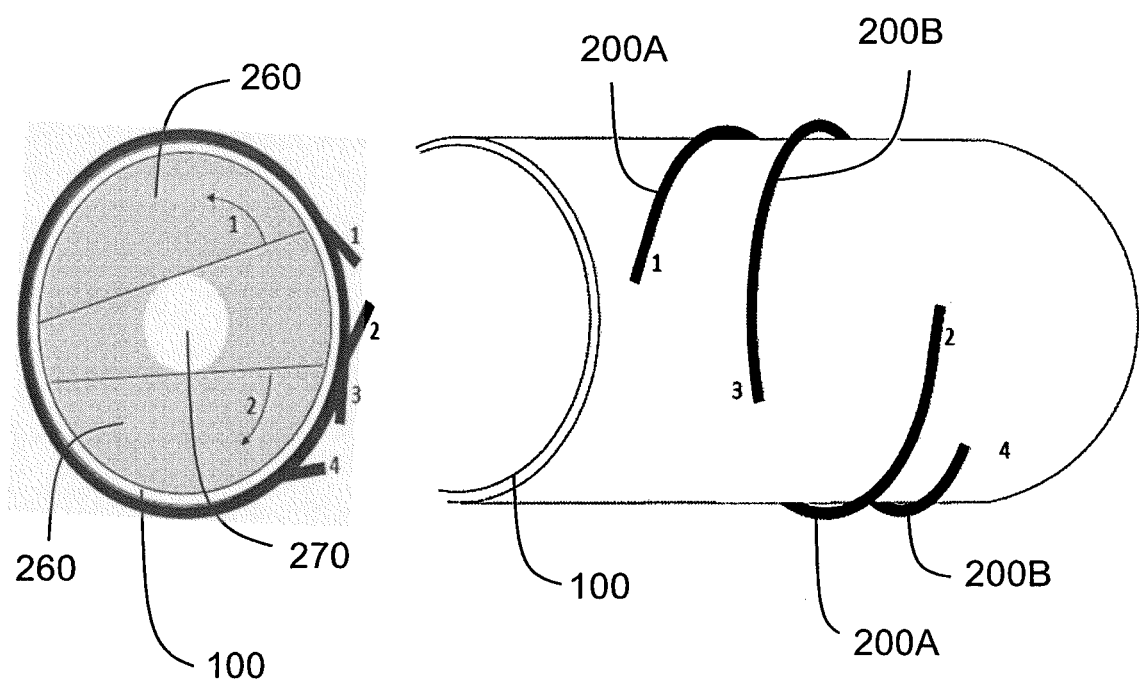
Figure 22:
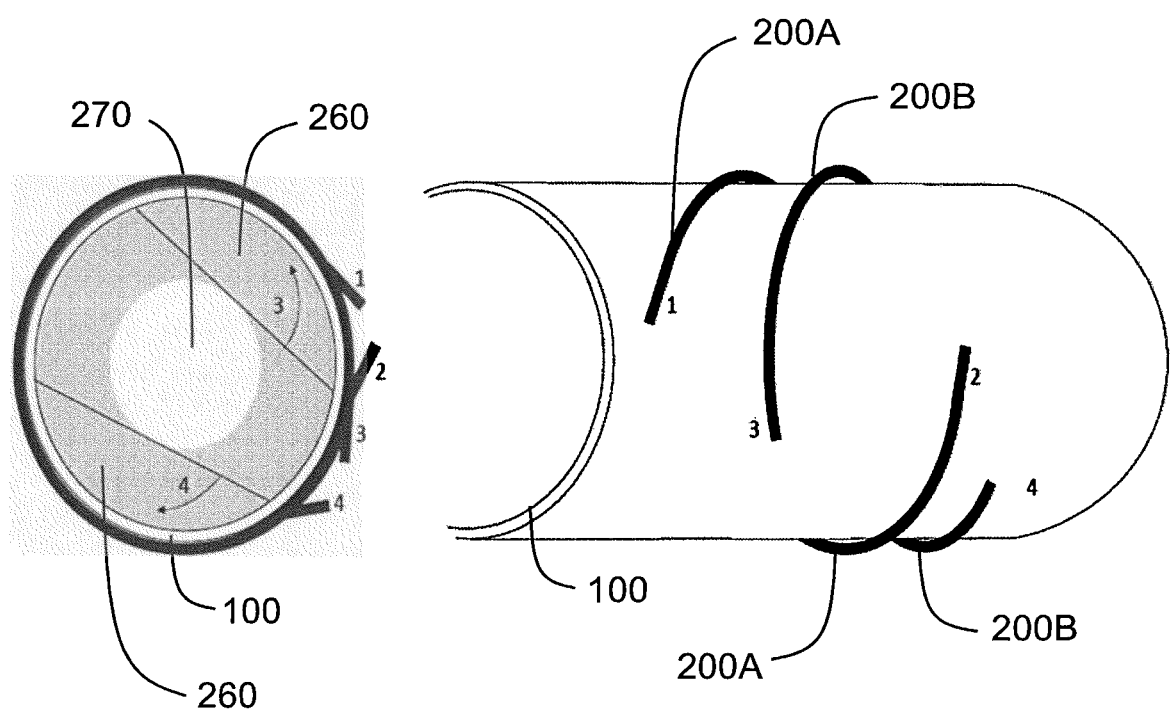
Figure 23:
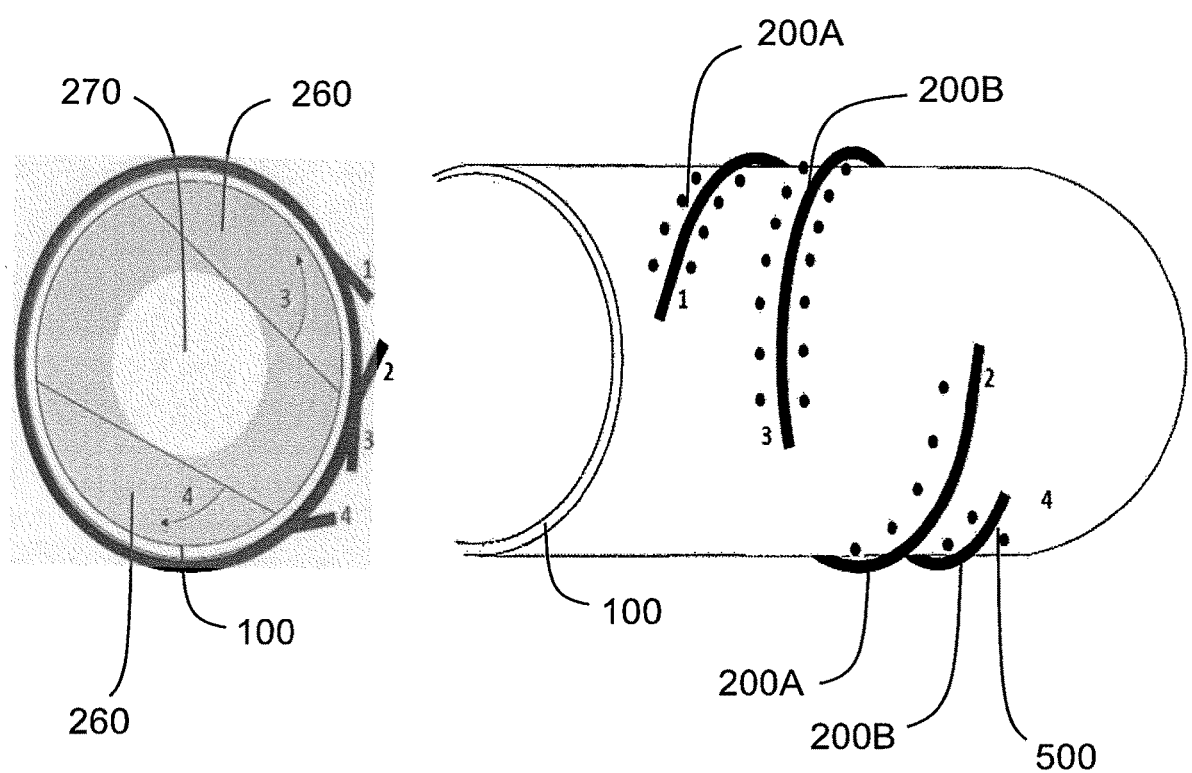

Referring next to FIGS. 21 to 23, the waveguides 200A, 200B are illustrated to encircle substantially 360° around the conduit 100 in a helical manner. Moreover, the waveguide 200A, 200B are illustrated as being mutually adjacent, and being mutually angularly displaced by circa 45°. The waveguides 200A, 200B are beneficially provided with associated Bragg-filter-grating sensors, denoted by 500, for sensing acoustic radiation; these sensors 500 are beneficially coupled directly to the external surface of the wall of the conduit 100, in a manner as described in the foregoing, In FIGS. 21 to 23, changing the radius of the "circle of construction" 270 by varying a size of sector addressed by the waveguides 200A, 200B is beneficially employed in tomographic (tomometric) imaging and analysis executed within the sensor apparatus 180, as described in the foregoing.

Figure 24:
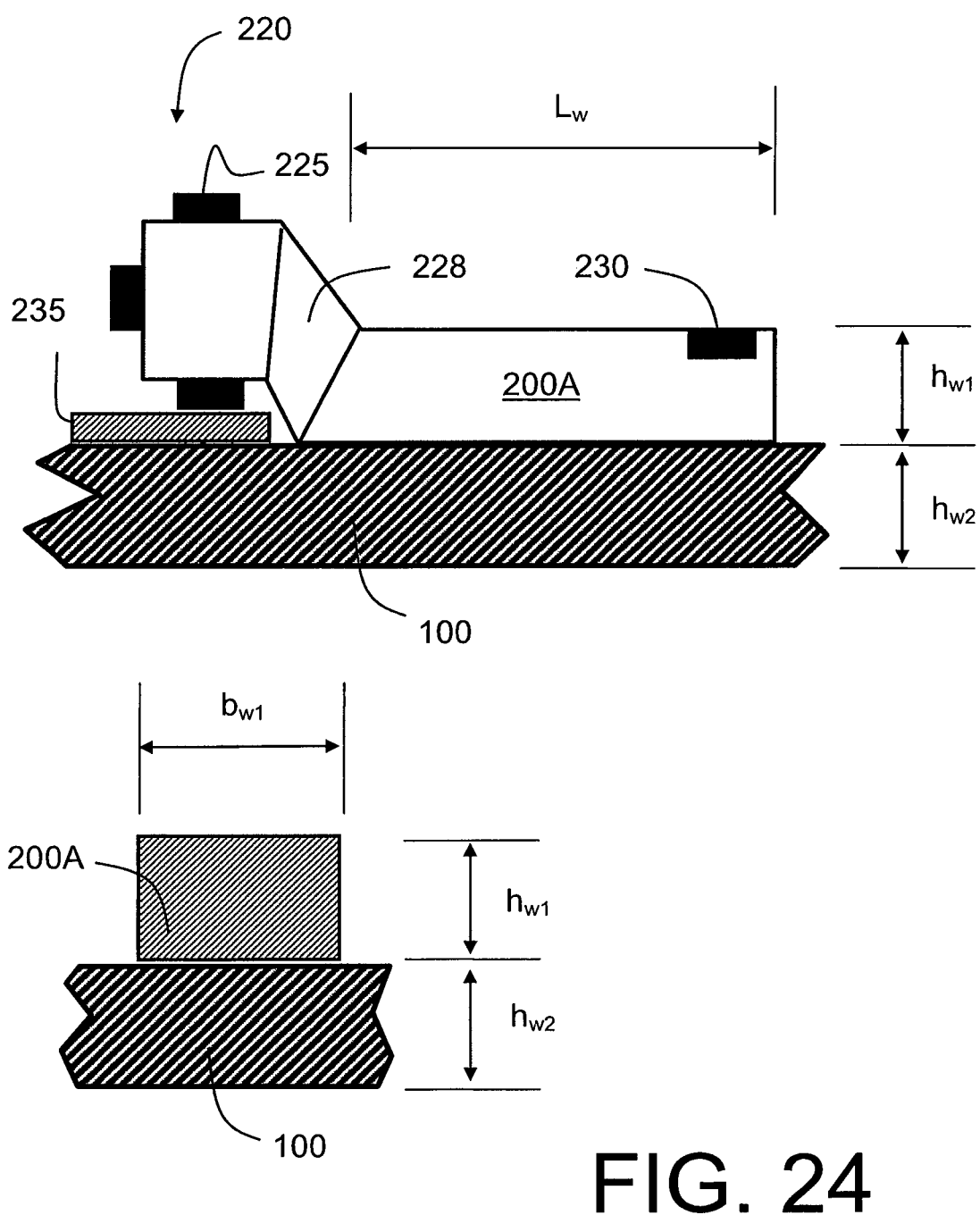

Referring next to FIG. 24, there is shown a detailed diagram of an example of the transducers 200, wherein the transducer 200 is shown mounted to an external surface of the wall of the conduit 100. The transducer includes an elongate waveguide 200A which is susceptible to being implemented in several ways, for example:

(a) as an elongate helix for exciting one or more helical modes of acoustic wave propagation within the wall of the conduit 100;

(b) as a substantially straight bar, a strip, an elongate plate, a flared plate;

(c) as a curved straight bar, a strip, an elongate plate;

(d) as a collar, as a flared collar; and (e) as an annulus.

The waveguide 200A has a thickness $h_{w1}$ which is substantially similar to a thickness $h_{w2}$ of a wall of the conduit 100 to which the waveguide 200A is mounted. Beneficially, the waveguide 200A is fabricated from a substantially similar material to that of the wall of the conduit 100, or from a material which has substantially similar material mechanical characteristics to that of the wall of the conduit 100. The waveguide 200A is beneficially manufactured from a metal, an alloy, a sintered material, a ceramic material, a composite material, a piezoelectric ceramic material, but not limited thereto. Moreover, the waveguide 200A is optionally integral with the wall of the conduit 100, for example machined from a mutually common component. Furthermore, the waveguide 200A is optionally a clamp-on device wherein a coupling cement, adhesive or gel is optionally used to provide an acoustic interface from the waveguide 200A to the wall of the conduit 100.

The waveguide 200A optionally has a height:length aspect ratio, namely $L_{w1}:h_{w1}$ ratio, in a range of 1.5:1 to 20:1, more optionally in a range of 2:1 to 10:1. Moreover, the the waveguide 200A beneficially has a width:height ratio, namely $b_{w1}:h_{w1}$ in a range of 2:1 to 1:100, and more optionally in a range of 1:1 to 1:20.

The waveguide 200A is coupled via a neck region 228 to a distal end indicated generally by 220. At the distal end 220, there is mounted, or otherwise provided, a cluster of elements 225, wherein at least one element is included on an end face of the distal end, as shown, and one or more elements are included on one or more side faces of the distal end as illustrated. Optionally, elements are mounted on a plurality of side faces of the distal end, as illustrated. The elements are beneficially implemented as piezoelectric elements when the transducer is required to excite acoustic radiation. When the transducer is to receive acoustic radiation, the elements 225 are optionally implemented as piezoelectric receiver elements and/or optical fibre Bragg-grating sensors.

The element at the end face of distal end is selective excited in operation to excite shear waves within the waveguide 200A. When the element on an upper or lower side face of the distal end is excited at relatively high frequencies, for example in an order of 1 MHz, Rayleigh are excited in operation within the waveguide 200A. Moreover, when a combination of drive signals is applied to the element at the end face of the distal end and to one or more of the elements at side faces of the distal end, a steerable mode is generated within the waveguide 200A, which can be used to generate a steerable beam of radiation within the volume 260 of the conduit 100, or confined to the wall of the conduit 100 in a steerable manner. Such multimode operation of the waveguide 200A is not feasible with known types of ultrasonic transducers which are predominantly shear mode type transducers.

The neck region 228 is beneficially considerable shorter than the waveguide 200A itself, for example at least five times shorter. Optionally, the distal end is raised, as illustrated, to enable a shield 235 to be inserted between the distal end and the outer surface of the wall of the conduit 100. The shield 235 is beneficially a thermal shield and/or ionizing radiation shield. When a thermal shield is required, the shield 235 is beneficially implemented as a multilayer structure including reflective electrical conductive layers, for example fabricated from metal film, grapheme film or similar, sandwiched between dielectric layers. Alternatively, when ionizing radiation shielding is required, the shield 235 is fabricated from a material including radiation absorbers such as lead, bismuth, boron, xenon, or similar; xenon is absorbed into interstitial spaces in certain materials and becomes physically trapped in interstitial spaces; for ionizing radiation shielding, silicon carbide is beneficially employed as a structural component of the shield 235, on account of its ability mechanically to resist neutron embrittlement.

The waveguide 200A is also provided with a sensor arrangement 230 for monitoring acoustic modes that are excited within the waveguide 200A, when in operation. The sensor arrangement 230 is optionally implemented using one or more piezoelectric elements or Bragg-grating sensors, as described in the foregoing. The Bragg-grating sensors are beneficially included a mutually common optical fibre which is formed in multiple pigtail loops for provided a linear array of sensor elements for the sensor arrangement; this represents a particularly compact and effect manner of implementing the sensor arrangement 230. The sensor arrangement 230 enables corrections to be made to mode steering direction and/or mode amplitude, for example for errors arising from gradual depolarization of the piezoelectric elements disposed at the distal end of the waveguide 200A.

Figure 25:
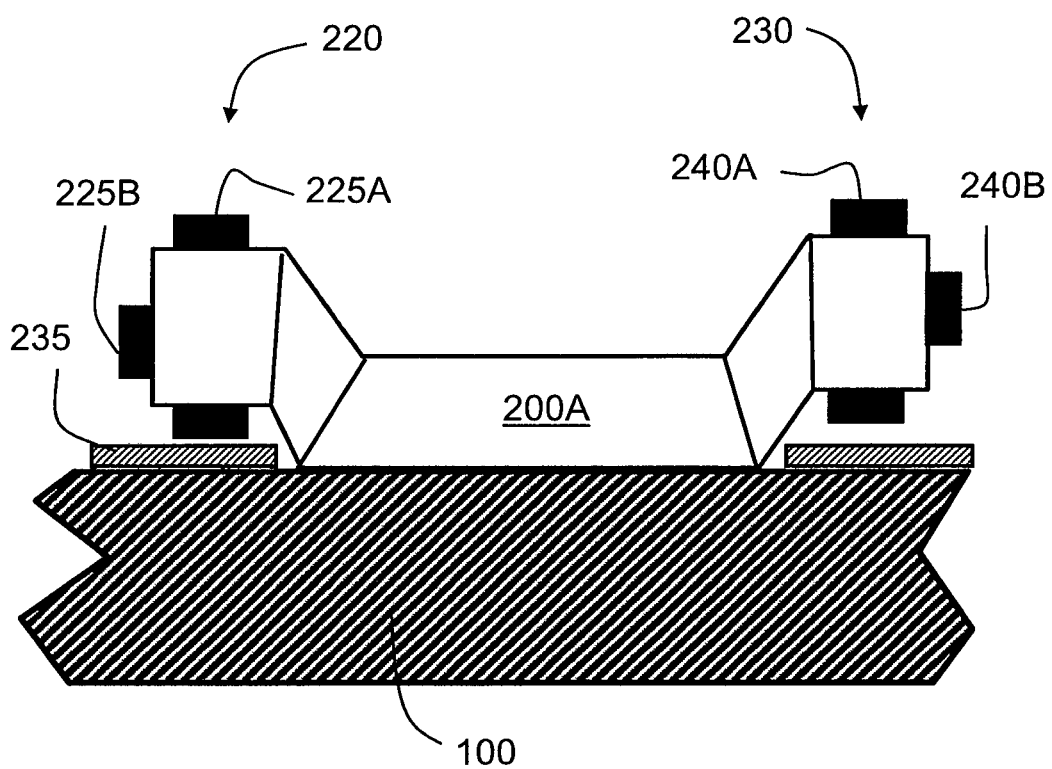

Referring next to FIG. 25, the waveguide 200A is beneficially implemented in a symmetrical manner, wherein a first distal end includes the elements 225 for exciting acoustic radiation, for example an element 225B at an end face of the first distal end and an element 225A on a side upper face of the first distal end, and a second distal end includes a similar arrangement of elements 240, for example an element 240B at an end face of the second distal end and an element 240A on a side upper face of the first distal end. As aforementioned, these elements are beneficially driven selectively at the first distal end to excite selected acoustic modes, and monitored at the second distal end to verify an amplitude and steering direction of the excited acoustic radiation in the waveguide 200A. Optionally, the first and second distal ends are raised away from the external surface of the conduit 100 to enable the shield 235 to be interposed for providing shielding for the elements.

Figure 26:
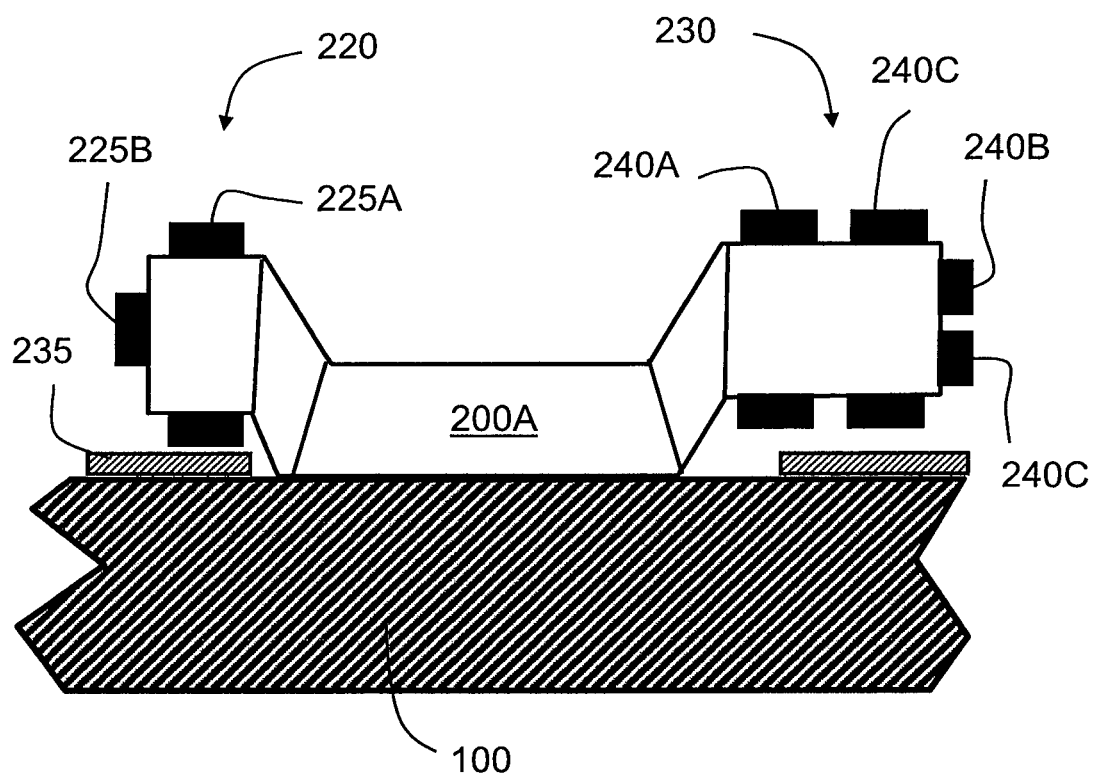

Referring next to FIG. 26, the waveguide 200A is further provided with an active acoustic damping arrangement at the second distal end, wherein the elements 240A and 240B are employed to sense acoustic modes generated by the elements 225 within the waveguide 220A, and the elements 240C, for example implemented as piezoelectric elements, are driven with selected anti-phase drive signals for dampening reflection of acoustic radiation being reflected at the end face of the second distal end which could otherwise cause formation of a standing wave mode within the waveguide 200A between the end faces of the first and second distal ends. Optionally, passive damping materials are added at the second distal end to dampen reflection of radiation from end faces of the first and second distal ends; such damping materials include, for example elastic polymeric material, resins, waxes, gels and similar.

As aforementioned, the waveguide 200A can be shaped as an elongate strip, a helical strip, a flat plate, a flared plate, a curved plate, a collar, a flared collar, an annulus, or similar. Moreover, the waveguide 200A is optionally shaped so as to be capable of supporting only a limited number of different acoustic modes, for example by making it long relative to its width, and having a low aspect ratio for its height relative to its breadth. Alternatively, the waveguide 200A can be implemented as a broad strip which is capable of supporting a large number of acoustic modes, when a higher degree of acoustic mode steerability is required. Optionally, the waveguide 200A is tapered along its length, between its one or more necks 228, namely a principal length $L_{w1}$ of the waveguide 200A. Alternatively, the waveguide 200A can have a substantially constant cross-section along its length, between its one of more necks 228.

Figure 27:
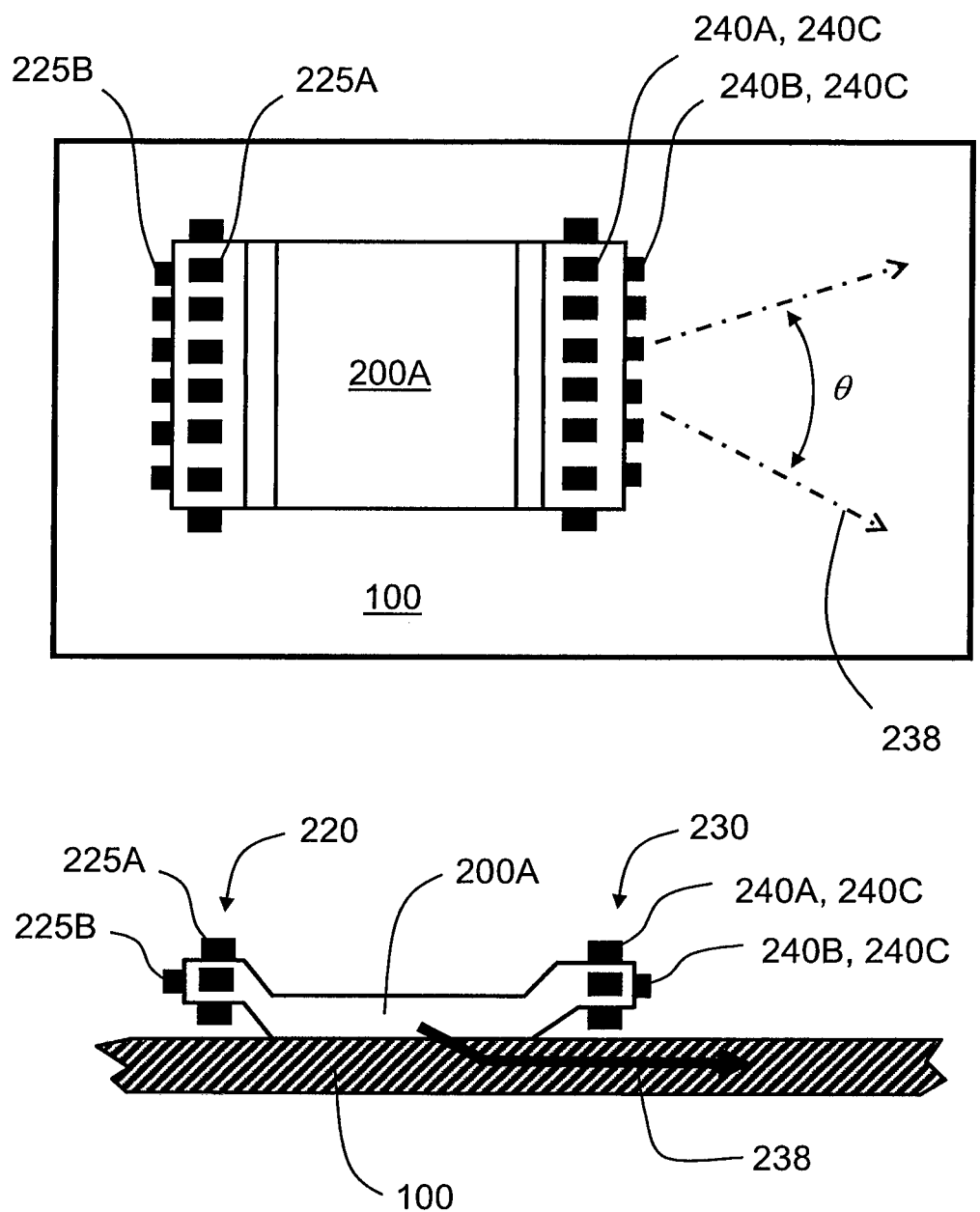

Referring to FIG. 27, there is provided an illustration of the waveguide 200A as a broad strip, wherein the elements 225 are implemented as a phased array for enabling an excited mode of acoustic radiation 238 to be steered in a range of angles θ, by varying at least one of:

(a) a frequency of drive signals applied in operation to the elements 225;

(b) a relative phase of drive signals applied in operation to the elements 225; and (c) a relative amplitude of drive signals applied in operation to the elements 225

The waveguide 200A, is optionally broad and curved in form, for example for being detachable mountable to the conduit 100, and being operable to excite a beam of a mode of highly pure acoustic radiation for interrogating, for example the wall of the conduit 100, and optionally a region adjacent thereto.

Modifications to embodiments of the invention described in the foregoing are possible without departing from the scope of the invention as defined by the accompanying claims. For example optionally in an embodiment the spatially attenuation is most commonly measured for a signal that has passed through the gas volumes 700 present in the region 260 and not only along the wall of the conduit 100.

Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

We claim:

1. A flow sensor apparatus, comprising:
 a transducer arrangement arranged to be non-invasively disposed at least partially around an external surface of a wall of a conduit for guiding a flow, wherein
 the transducer arrangement is operable to stimulate waves in off-centre chordal paths within the flow, wherein the stimulated waves in the off-centre chordal paths that interact with the flow include information which characterizes off-centre properties of the flow;
 the transducer arrangement is operable to excite helically propagating acoustic Lamb waves within the wall of the conduit and stimulate the waves of the off-centre chordal paths within the flow by leaking acoustical energy from the helically propagating acoustic Lamb waves; and
 the transducer arrangement is operable to receive the waves of the off-centre chordal paths, helically re-entering the wall of the conduit, and further propagating helically as guided acoustic Lamb waves into the transducer arrangement.

2. The sensor apparatus as claimed in claim 1, wherein the transducer arrangement includes an elongate waveguide arrangement which is operable to support an acoustic Lamb wave propagation therein from one or more driver elements disposed at one or more ends of the waveguide arrangement.

3. The sensor apparatus as claimed in claim 2, wherein the waveguide arrangement has at least one of its ends implemented as at least one free end, and the waveguide arrangement includes an acoustic radiation damping arrangement for dampening back-and-forth acoustic wave propagation along the waveguide arrangement.

4. The sensor apparatus as claimed in claim 1, wherein the elongate waveguide arrangement includes a waveguide for interfacing to the wall of the conduit, whose thickness and waveguide material are mutually substantially similar to a thickness and a material of the wall of the conduit, and wherein the waveguide is, implemented as a sheet, a collar, a helical elongate member, a helical strip, or a structure formed integrally into the wall of the conduit.

5. The sensor apparatus as claimed in claim 1, wherein the transducer arrangement includes one or more sensors which are implemented optically using one or more optical fibres, wherein one or more Bragg gratings are including along the one or more optical fibres for rendering the one or more optical fibres sensitive, and the one or more optical fibres are implemented using at least one of: one or more fused silica optical fibres, one or more sapphire optical fibres.

6. The sensor apparatus as claimed in claim 2, wherein the transducer arrangement is detachable from the wall of the conduit.

7. The sensor apparatus as claimed in claim 1, wherein the transducer arrangement is operable to interrogate a plurality of off-centre sectors of an interior volume of the conduit, and wherein an extent of the off-centre sectors defines an annular region in which the sensor apparatus is operable selectively to measure off-centre properties of the flow.

8. The sensor apparatus as claimed in claim 7, wherein the off-centre sectors are determined in spatial extent by a steering direction and/or a frequency of modes which are excited in operation by the transducer arrangement.

9. The sensor apparatus as claimed in claim 1, wherein the sensor apparatus further includes a data processing arrangement for providing driver signals to the transducer arrangement and for receiving signals from the transducer arrangement, wherein the data processing arrangement is operable to perform at least one of:
 (a) at least one spatial measurement of at least one of a liquid or gas phase present within the conduit;
 (b) at least one flow measurement of the at least one of the liquid or gas phase present within the conduit;
 (c) a spatial tomographic imaging of one or more sectors interrogated by the transducer arrangement;
 (d) a Doppler flow measurement of bubbles present within the conduit;
 (e) a time-of-flight acoustic measurement through the at least one of the liquid or gas phase present in the conduit in operation, and along the wall of the conduit, in, downstream and upstream flow directions, wherein the acoustic measurement along the wall of the conduit is used to provide error compensation for the acoustic measurement performed through the at least one of the liquid or gas phase;
 (f) at least one measurement, wherein at least one of the transducer arrangements of a waveguide arrangement is operable both to send and to receive acoustic radiation to and from the conduit via use of pulse-echo interrogation of a flow within the conduit;
 (g) a computation, based on time-of-flight measurements, of fluid flow rate within the conduit, and/or a fluid sound speed within the conduit;
 (h) a computation to compensate for changing flow profiles and/or swirl occurring within the conduit;
 (i) a computation to characterized a stratified flow occurring within the conduit; and
 (j) a measurement of structural integrity of the wall of the conduit, for determining at least one of: scale deposit, hydrate formation, wall thinning, embrittlement of the wall, micro-cracking within the wall of the conduit.

10. A method of using a flow sensor apparatus for measuring within a region of a conduit for guiding a flow, wherein the sensor apparatus includes a transducer arrangement arranged to be non-invasively disposed at least partially around an external surface of a wall of a conduit, comprising:
 operating the transducer arrangement to stimulate waves in off-centre chordal paths within the flow, wherein the stimulated waves in the off-axis chordal paths that interact with the flow include information which characterizes off-centre properties of the flow;
 operating the transducer arrangement to excite helically propagating acoustic Lamb waves within the wall of the conduit and stimulate the waves of the off-centre chordal paths within the flow by leaking acoustical energy from the helically propagating acoustic Lamb waves; and
 operating the transducer arrangement to receive the waves of the off-centre chordal paths, helically re-entering the wall of the conduit, and further propagating helically as a guided acoustic Lamb waves into the transducer arrangement.

11. The method as claimed in claim 10, wherein the method includes arranging for the transducer arrangement to include an elongate waveguide arrangement which is operable to support an acoustic Lamb wave propagation therein from one or more driver elements disposed at one or more ends of, the waveguide arrangement.

12. The method as claimed in claim 11, wherein the method includes arranging for the waveguide arrangement to have at least one of its ends implemented as at least one free end, and the waveguide arrangement to include an acoustic radiation damping arrangement for dampening back-and-forth acoustic wave propagation along the waveguide arrangement.

13. The method as claimed in claim 10, wherein the method includes arranging for the elongate waveguide arrangement to include a waveguide for interfacing to the wall of the conduit, whose thickness and waveguide material are mutually substantially similar to a thickness and a material of the wall of the conduit, wherein the waveguide is implemented as a sheet, a collar, a helical elongate member, a helical strip, or a structure formed integrally into the wall of the conduit.

14. The method as claimed in claim 10, wherein the method includes arranging for the transducer arrangement to include one or more sensors which are implemented optically using one or more optical fibres, wherein one or more Bragg gratings are including along the one or more optical fibres for rendering the one or more optical fibres sensitive, and the one or more optical fibres are implemented using at least one of: one or more fused silica optical fibres, one or more sapphire optical fibres.

15. The method as claimed in claim 11, wherein the transducer arrangement is detachable from the wall of the conduit.

16. The method as claimed in claim 11, wherein the method includes operating the transducer arrangement to interrogate a plurality of off-centre sectors of an interior volume of the conduit, wherein an extent of the off-centre sectors defines an annular region in which the sensor apparatus is operable selectively to measure off-centre properties of the flow.

17. The method as claimed in claim 16, wherein the off-centre sectors are determined in spatial extent by a steering direction and/or a frequency of modes which are excited in operation by the transducer arrangement.

18. The method as claimed in claim 10, wherein the sensor apparatus further includes a data processing arrangement for providing driver signals to the transducer arrangement and for receiving signals from the transducer arrangement, wherein the method includes arranging for the data processing arrangement to be operable to perform at least one of:
(a) at least one spatial measurement of at least one of a liquid or gas phase present within the conduit;
(b) at least one flow measurement of the at least one of the liquid or gas phase present within the conduit;
(c) a spatial tomographic imaging of one or more sectors interrogated by the transducer arrangement;
(d) a Doppler flow measurement of bubbles present within the conduit;
(e) a time-of-flight acoustic measurement through the at least one of the liquid or gas phase present in the conduit in operation, and along the wall of the conduit, in downstream and upstream flow directions, wherein the acoustic measurement along the wall of the conduit is used to provide error compensation for the acoustic measurement performed through the at least one of the liquid or gas phase;
(f) at least one measurement, wherein at least one of the transducer arrangements of a waveguide arrangement is operable both to send and to receive acoustic radiation to and from the conduit via use of pulse-echo interrogation of a flow within the conduit;
(g) a computation, based on time-of-flight measurements, of fluid flow rate within the conduit, and/or a fluid sound speed within the conduit;
(h) a computation to compensate for changing flow profiles and/or swirl occurring within the conduit;
(i) a computation to characterized a stratified flow occurring within the conduit; and
(j) a measurement of structural integrity of the wall of the conduit, for determining at least one of: scale deposit, hydrate formation, wall thinning, embrittlement of the wall, micro-cracking within the wall of the conduit.

19. A computer program product comprising a non-transitory computer-readable storage medium having computer-readable instructions stored thereon, the computer-readable instructions being executable by a computerized device comprising processing hardware to perform the actions of:
with a flow sensor arrangement including a transducer arrangement arranged to be non-invasively disposed at least partially around an external surface of a wall of a conduit, measuring within a region of a conduit for guiding a flow;
operating the transducer arrangement to stimulate waves in off-centre chordal paths within the flow, wherein the stimulated waves in the off-axis chordal paths that interact with the flow include information which characterizes off-centre properties of the flow;
operating the transducer arrangement to excite helically propagating acoustic Lamb waves within the wall of the conduit and stimulate the waves of the off-centre chordal paths within the flow by leaking acoustical energy from the helically propagating acoustic Lamb waves; and
operating the transducer arrangement to receive the waves of the off-centre chordal paths, helically re-entering the wall of the conduit, and further propagating helically as a guided acoustic Lamb waves into the transducer arrangement.

* * * * *